US007708065B2

(12) United States Patent
Hendrickson et al.

(10) Patent No.: US 7,708,065 B2
(45) Date of Patent: May 4, 2010

(54) **IDENTIFICATION, CHARACTERIZATION, AND APPLICATION OF *THAUERA* SP. AL9:8 USEFUL IN MICROBIALLY ENHANCED OIL RECOVERY**

(75) Inventors: Edwin R. Hendrickson, Hockessin, DE (US); Raymond E. Jackson, Newark, DE (US); Sharon Jo Keeler, Bear, DE (US); Abigail K. Luckring, West Chester, PA (US); Michael P. Perry, Landenberg, PA (US); Sheryl Wolstenholme, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/240,205

(22) Filed: Sep. 29, 2008

(65) Prior Publication Data

US 2010/0078162 A1   Apr. 1, 2010

(51) Int. Cl.
*E21B 43/22* (2006.01)
*C09K 8/582* (2006.01)

(52) U.S. Cl. ........................... 166/246; 507/201
(58) Field of Classification Search ............. None
See application file for complete search history.

(56) References Cited

U.S. PATENT DOCUMENTS

| 4,717,653 | A | 1/1988 | Webster, Jr. et al. |
| 5,877,014 | A | 3/1999 | Shetty et al. |
| 6,087,155 | A | 7/2000 | York et al. |
| 6,573,087 | B2 | 6/2003 | Lehr |

OTHER PUBLICATIONS

S. A. Kianipey et al., 61st Annual Technical Conference and Exhibition, 1986, pp. 1-13, New Orleans, LA, USA.
L. R. Brown et al., J. SPE 59306, SPE/DOE Improved Oil Recovery Symposium, 2000, pp. 1-16, Oklahoma.
E. Sunde et al., SPE 24204, SPE/DOE 8th Symposium on Enhanced Oil Recovery, 1992, pp. 497-502.
Mechichi et al., Phylogenetic and Metabolic Diversity of Bacteria Degrading Aromatic Compounds Under Denitrifying Conditions, and Description of *Thauera phenylacetica* sp. nov., *Thauera aminoaromatica* sp. nov., and *Azoarcus buckelii* sp. nov., Arch. Microbiol., 2002, vol. 178:26-35.
Anders et al., Taxonomic Position of Aromatic-Degrading Denitrifying Pseudomonad Strains K 172 and KB 740 and Their Description as New Members of the Genera *Thauera*, as *Thauera aromatica* sp. nov., and *Azoarcus*, as *Azoarcus evansii* sp. nov., Respectively, Members of the Beta Subclass of the *Proteobacteria*, Int. J. Syst. Evol. Microbiol., 1995, vol. 45:327-333.
Verfurth et al., Substrate Specificities and Electron Paramagnetic Resonance Properties of Benzylsuccinate Synthases in Anaerobic Toluene and M-Xylene Metabolism, Arch. Microbiol., 2004, vol. 181:155-162.
Boll et al., Anaerobic Oxidation of Aromatic Compounds and Hydrocarbons, Curr. Op. Chem. Biol., 2002, vol. 6:604-611.

National Center for Biotechnology Information General Identifier No. CR555306.1, Nov. 14, 2006, R. Rabus et al., Genes Involved in the Anaerobic Degradation of Ethylbezene in a Denitrifying Bacterium, Strain EBN1.
Altschul et al., Basic Local Alignment Search Tool. J. Mol. Biol., 1990, vol. 215:403-410.
W. R. Pearson, Searching Protein Sequence Databases—Is Optimal Best?, Comput. Methods Genome Res., Proc. Int. Symp, 1992, pp. 111-120.
National Center for Biotechnology Information General Identifier No. AY945908.1, Jan. 28, 2006, B. Liu et al., Direct Submission.
National Center for Biotechnology Information General Identifier No. AJ315680.1, Jul. 5, 2002, T. Mechichi et al., Phylogenetic and Metabolic Diversity of Bacteria Degrading Aromatic Compounds Under Denitrifying Conditions, and Description of *Thauera phenylacetica* sp. nov., *Thauera aminoaromatica* sp. nov., and *Azoarcus buckelii* sp. nov.
D. A. Newcombe et al., Bioremediation of Atrazine-Contaminated Soil by Repeated Applications of Atrazine-Degrading Bacteria, Appl. Microbiol. Biotechnol., 1999, vol. 51:877-882.
C. Barbeau et al., Bioremediation of Pentachlorophenol-Contaminated Soil by Bioaugmentation Using Activated Soil, Appl. Microbiol. Biotechnol., 1977, vol. 48:745-752.
Dorobantu et al., Stabilization of Oil-Water Emulsions by Hydrophobic Bacteria, Appl. Environ. Biol., 2004, vol. 70:6333-6336.
V. Pruthi et al., Rapid Identification of Biosurfactant—Producing Bacterial Strains Using a Cell Surface Hydrophobicity Technique, Biotechnol. Techniques, 1997, vol. 11:671-674.
C. Moreno-Vivian et al., Prokaryotic Nitrate Reduction: Molecular Properties, and Functional Distinction Among Bacterial Nitrate Reductases, J. Bacteriol., 1999, vol. 181:6573-6584.
J. L. Bruce, Automated System Rapidly Identifies and Characterizes Microorganisms in Food, Food Techno., 1996, vol. 50:77-81.
M. R. Sethi, Fully Automated Microbial Characterization and Identification for Industrial Microbiologists, Am. Lab., 1997, vol. 5:31-35.
Beller et al., A Real-Time Polymerase Chain Reaction Method for Monitoring Anaerobic, Hydrocarbon-Degrading Bacteria Based on a Catabolic Gene, Environ. Sci. Technol., 2002, vol. 36:3977-3984.
B. Liu et al., *Thauera* and *Azoarcus* Functionally Important Genera in a Denitrifying Quinoline-Removal Bioreactor as Revealed by Microbial Community Structure Comparison, FEMS Microbiol. Ecol., 2006, vol. 55:274-286.
National Center for Biotechnololgy Information General Identifier No. YP_160313 (56478724), Jan. 21, 2009, S. Kuhner et al., Substrate-Dependent Regulation of Anaerobic Degradation Pathways for Toluene and Ethylbenzene in Denitrifying Bacterium, Strain EBN1.
National Center for Biotechnology Information General Identifier No. YP_158333.1 (56476744), Jan. 21, 2009, S. Kuhner et al., Substrate-Dependent Regulation of Anaerobic Degradation Pathways for Toluene and Ethylbenzene in Denitrifying Bacterium, Strain EBN1.
National Center for Biotechnology Information General Identifier No. AAK76387.1 (14994027), Jul. 22, 2001, H. A. Johnson et al., Isolation and Characterization of Anaerobic Ethylbenzene Dehydrogenase, a Novel MO-FE-S Enzyme.

*Primary Examiner*—Zakiya W. Bates

(57) ABSTRACT

The present disclosure relates to isolation, identification and application of *Thauera* strain AL9:8 which grows on crude oil as the sole carbon source under denitrifying anaerobic conditions *Thauera* strain AL9:8 can be used alone or in concert with other microorganisms to improve oil recovery, bioremediation of oil or hydrocarbons in contaminated soil, ground water or bodies of water, such as lakes, rivers or oceans and/or applying to method for promoting oil pipeline maintenance, removing a build up hydrocarbon on the intersurfaces of the pipeline.

12 Claims, 8 Drawing Sheets

At 7 Days

At 3 Months

Figure 1A:
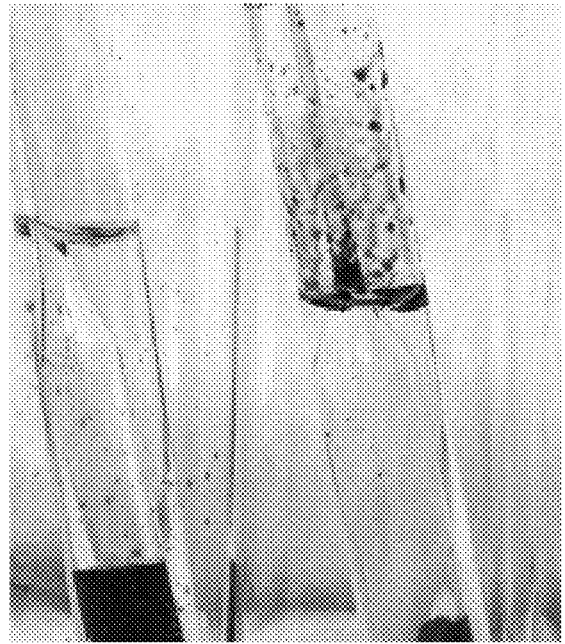

```
Thauera AL9.8 profile    335 ACTCCTACGGGAGGCAGCAGTGGGGAATTTTGGACAATGGGCGCAAGCCTGATCCA 386
                             340       350       360       370       380       390
                             ---------+---------+---------+---------+---------+------

Thauera AL9.8                ACTCCTACGGGAGGCAGCAGTGGGGAATTTTGGACAATGGGCGCAAGCCTGATCCA 318
Clone DR-7 AY945908          ACTCCTACGGGAGGCAGCAGTGGGGAATTTTGGACAATGGGCGCAAGCCTGATCCA 382
Thauera aromatica LG356(AJ315680) ACTCCTACGGGAGGCAGCAGTGGGGAATTTTGGACAATGGGCGCAAGCCTGATCCA 370
Thauera aromatica S100       ACTCCTACGGGAGGCAGCAGTGGGGAATTTTGGACAATGGGCGCAACCCTGATCCA 364
Thauera sp. T1               ACTC-TACGGGAGGCAGCAGTGGGGAATTTTGGACAATGGGGGCAACCCTGATCCA 381
Thauera sp. mzlt             ATTCCTACGGGAAGCAGCAGTGGGGAATTTTGGACAATGGGCGCAAGCCTGATCCA 385
Azoarcus BH72                ACTCCTACGGGAGGCAGCAGTGGGGAATTTTGGACAATGGGCGAAAGCCTGATCCA 386
```

FIG. 2A

*Thauera sp AL9.8* profile of the signature sequences in bacterial variable region 6

```
Thauera AL9.8 profile    995 ATGCCAGGAACCTTGCCGAGAGGCGAGGGTGCCTTCGGGAGCCTG 1034
                             ---------+---------+---------+---------+-----

Thauera AL9.8                ATGCCAGGAACCTTGCCGAGAGGCGAGGGTGCCTTCGGGAGCCTG 966
Clone DR-7 AY945908          ATGCCAGGAACCTTGCCGAGAGGCGAGGGTGCCTTCGGGAGCCTG 1030
Thauera aromatica LG356(AJ315680) ATGCCAGGAACCTTGCCGAGAGGCGAGGGTGCCTTCGGGAGCCTG 1018
Thauera aromatica S100       ATGCCAGGAACCTTGCTGAGAGGCGAGGGTGCCTTCGGGAGCCTG 1011
Thauera sp. T1               ATGCCAGGAACCTTGCTGAGAGGCGAGGGTGCCTTCGGGAGCCTG 1028
Thauera sp. mzlt             ATGTCTGGAACCTTGCTGNGAGGCGAGGGTGCCTTCGGGAGCCAG 1034
Azoarcus BH72                ATGCCTGGAACCTTGGTGAGAGCCGAGGGTGCCTTCGGGAACCAG 1034
```

FIG. 2B

```
Tha  9:8:   1 RRKFLKGSGG LCLSLSLSSF APGFVPGVVS EALAGTKVPS YAKWEDIYRN EWKWDKVTWG  60
              RR•FLK•SG• ••LSLSLSSF A•G•VPG•V+ •A•AG••+P+ YA•WED+YRN EWKWDKVTWG
Az EbN1:   22 RRGFLKRSGA GALSLSLSSF AAGLVPGFVN AAQAGKRGPT YATWEDVYRN EWKWDKVTWG  81

Tha  9:8:  61 SHLNICWPQG SCKFYVYVRN GIVWREEQAA QTAACNADYV DYNPLGCQKG AAFNNNLYGD 120
              SHLNICWPQG SCKFYVYVRN GIVWREEQAA QTAACN•DYV DYNP•GCQKG AAFNNNLYG+
Az EbN1:   82 SHLNICWPQG SCKFYVYVRN GIVWREEQAA QTAACNPDYV DYNPSGCQKG AAFNNNLYGE 141

Tha  9:8: 121 ERVK

```
Tha 9:8:  301  DRKFVSEQT  DLPLLVRTDNG  KFLSAADVDG  GHEKQFYVID  EKSGAMRQAP  RGTLRLDGPV  360
               DR+F·SEQT  DLPLLVRTDNG  KFLSAADVDG  GH·KQFYVID  EKSGA+R+AP  RGTLRLDGPV
Az EbN1: 322  DRQFASEQT  DLPLLVRTDNG  KFLSAADVDG  GHAKQFYVID  EKSGALREAP  RGTLRLDGPV  381

Tha 9:8:  361  ALEGTFKAK  LRDGKTVEVRP  VFQMMKDQLE  QEFTPEKASE  KSGVPVSLIR  ELGRKVAKKR  420
               ALEGTF·AK  LRDG·TV+VRP  VFQ+MKDQL+  +EFTPEKAS·  KSG·P·SLIR  ELGRKVAKKR
Az EbN1: 382  ALEGTFSAK  LRDGGTVQVRP  VFQLMKDQLD  KEFTPEKASA  KSGAPASLIR  ELGRKVAKKR  441

Tha 9:8:  421  TSTYIGFTA  AKSYHGDLFER  AMYLALALSG  NWGKPGTGFY  SWAYAEDNMF  FLSVMNKPTA  480
               TS+YIGFTA  AKSYHGDLFER  +MYLA+ALSG  NWGKPGTGFY  SWAYAEDNMF  FL+VMNKPTA
Az EbN1: 442  TSSYIGFTA  AKSYHGDLFER  SMYLAMALSG  NWGKPGTGFY  SWAYAEDNMF  FLAVMNKPTA  501

Tha 9:8:  481  QGGMDEMAQ  MQKSFHDRLKK  EDPTSTDEMA  DIEFTKAVTT  L  521
               QGGM+EMA+  MQKSFH+RLKK  ·DPTSTDEMA  DIEFTKAVTT  L
Az EbN1: 502  QGGMNEMAE  MQKSFHERLKK  GDPTSTDEMA  DIEFTKAVTT
```

FIG. 3B

IDENTIFICATION, CHARACTERIZATION, AND APPLICATION OF *THAUERA* SP. AL9:8 USEFUL IN MICROBIALLY ENHANCED OIL RECOVERY

FIELD OF INVENTION

This disclosure relates to the field of environmental microbiology and modification of heavy crude oil properties using microorganisms. More specifically, pure microorganisms are used under denitrifying conditions to modify the properties of heavy crude oil resulting in enhanced recovery of the crude oil from its underground reservoir and bioremediation.

BACKGROUND OF THE INVENTION

The challenge to meet the ever-increasing demand for oil includes increasing crude oil recovery from heavy oil reservoirs. This challenge has resulted in expanding efforts to develop alternative cost efficient oil recovery processes (Kianipey, S. A. and Donaldson, E. C. 61$^{st}$ Annual Technical Conference and Exhibition, New Orleans, La., USA, Oct. 5-8, 1986). Heavy hydrocarbons in the form of petroleum deposits and oil reservoirs are distributed worldwide. These oil reservoirs are measured in the hundreds of billions of recoverable barrels. Because heavy crude oil has a relatively high viscosity, it is essentially immobile and cannot be easily recovered by conventional primary and secondary means. Thus there is a need for various methods to enhance bioremediation and oil recovery.

Microbial Enhanced Oil Recovery (MEOR) is a methodology for increasing oil recovery by the action of microorganisms (Brown, L. R., Vadie, A. A., Stephen, O. J. SPE 59306, SPE/DOE Improved Oil Recovery Symposium, Oklahoma, Apr. 3-5, 2000). MEOR research and development is an ongoing effort directed at discovering techniques to use microorganisms to modify crude oil properties to benefit oil recovery (Sunde E., Beeder, J., Nilsen, R. K. Torsvik, T., SPE 24204, SPE/DOE 8$^{th}$ Symposium on enhanced Oil Recovery, aerobic or anaerobic conditions (Mechichi Tahar et. al., Arch Microbiol., (2002), 178: 26-35 Tulsa, Okla., USA, Apr. 22-24, 1992). Thus, identifying microorganisms that could be used to enhance oil recovery under economic conditions, can grow on oil under anaerobic conditions without the need for nutrient supplementation or long term enrichment of indigenous microorganisms which can be used, in a cost-efficient way, to improve bioremediation is of significant importance.

Particular strains of denitrifying bacteria belonging to the Beta-Proteobacteria related genera, e.g., *Azoarcus* and *Thauera* have been shown to grow on oil and or oil constituents under anaerobic conditions without the need for nutrient supplementation (Anders et. al. Int. J. Syst. Evol. Microbiol., (1995), 45: 327-333). The anaerobic pathways involved in hydrocarbon metabolism have been studied in *Thauera* and *Azoarcus* species. An important class of enzymes in these pathways are benzylsuccinate synthases (bss), which catalyze the metabolism of simple aromatic compounds and are synthesized by the bss operon. These enzymes have been identified in *Thauera* and *Azoarcus* species and shown to possess varied substrate specificities. For example, while the bss enzyme of an *Azoarcus* strain converts toluene, all xylene and cresol isomers to the corresponding succinate adducts, the same enzyme from *Thauera aromatica* is active with toluene and all cresols, but not with any xylene isomers. Thus, differences in substrate specificity of the bss enzymes in these two denitrifying bacterial strains contributes to their varied ability in utilization of different aromatic hydrocarbons (Verfürth et al., Arch Microbiol., (2004), 181: 155-162). An additional pathway of anaerobic hydrocarbon catabolism has been reported in selected *Azoarcus* strains (i.e. strains EB1, and EbN1) but has not been identified in any *Thauera* strains to date. In this pathway, ethylbenzene and n-propylbenzene are oxidized under anaerobic conditions by the ethylbenzene dehydrogenase (ebd) enzyme (Boll, et al., Curr. Op. Chem. Biol., (2002), 6: 604-611)

Ultimately, most of the aromatic compounds are converted to the central intermediate benzoyl-CoA via different metabolic pathways, where they undergo enzymatic benzene ring cleavage via Benzoyl-CoA reductase (bcr) (Mechichi, et al., Arch. Microbiol. (2002), 178: 26-35). While similar enzymes are widely distributed among denitrifying bacteria much of the information reported to date is derived from a bcr enzyme isolated from *Thauera aromatica*.

This disclosure relates to a novel *Thauera* strain AL9:8, defined by its ability to grow on crude oil, and by the presence of a gene sequence derived from the ebdA-like gene hitherto unidentified in *Thauera* species. Thus the present disclosure, relates to both the identification and use of a microorganism that grows in the presence of crude oil, and modifies its physico-chemical properties to enhance bioremediation under denitrifying conditions.

SUMMARY OF THE INVENTION

The invention relates to the identification of a microorganism from samples obtained from an environmental site, which had been exposed to tar, creosol and polycyclic aromatic hydrocarbons (PAHs) to fulfill the needs identified above. Several enrichment cultures were developed as microcosms of microbes that grow on crude oil under denitrifying conditions. A screening protocol was then developed to isolate and identify pure strains capable of growth under denitrifying conditions using oil or oil components as the sole source of carbon. These microbes are capable of growing in situ in an oil reservoir for enhancement of oil recovery and bioremediation. Growth of these microorganisms, and specifically the pure cultures described herein, in an oil well or reservoir provides for economical recovery of oil.

One of the strains designated *Thauera* strain AL9:8, was confirmed to be a previously unidentified strain of the *Thauera* genus via ribotyping of the genomic sequences surrounding the 5S, 16S and 23S rRNA genes. Thus, one aspect of the present disclosure relates to an isolated microorganism designated as bacterial isolate *Thauera* strain AL9:8 (ATCC No. 9497).

Another aspect relates to an oil recovery enhancing composition comprising: a) *Thauera* strain AL9:8 (ATCC No. 9497); b) one or more electron acceptors; and c) one or more carbon sources such as acetate, succinate, lactate, benzoate or glucose. A further aspect relates to a method for improving oil recovery from an oil reservoir by: a) providing a composition of *Thauera* strain AL9:8 (ATCC No. 9497), and minimal medium comprising simple nitrates capable of promoting the growth of said isolate; and b) inoculating said reservoir with the composition of (a); wherein growth of said isolate, under denitrifying conditions, in the oil reservoir promotes improved oil recovery.

An additional aspect relates to a method for promoting oil recovery comprising applying *Thauera* strain AL9:8 (ATCC No. 9497) to an oil-contaminated area.

Another aspect relates to a method for promoting oil pipeline maintenance comprising applying *Thauera* strain AL9:8 (ATCC No. 9497) to an oil pipeline.

A further aspect is an isolated microorganism having substantially the same ribotyping profile as the bacterial isolate *Thauera* strain AL9:8 (ATCC No. PTA 9497).

INFORMATION ON DEPOSITED STRAIN

| Depositor Identification Reference | International Depository Designation | Date of Deposit |
|---|---|---|
| *Thauera* sp. strain AL9.8 | ATCC No. PTA-9497 | Sep. 17, 2008 |
| *Pseudomonas stutzeri* strain LH4:15 | ATCC PTA-8823 | Dec. 4, 2007 |

BRIEF DESCRIPTION OF FIGURES AND DNA AND PROTEIN SEQUENCES OF THE INVENTION

The preferred embodiments of the invention will hereinafter be described in conjunction with the appended drawings provided to illustrate, but not to limit the invention, wherein like designations denote like elements.

Figure 1B:
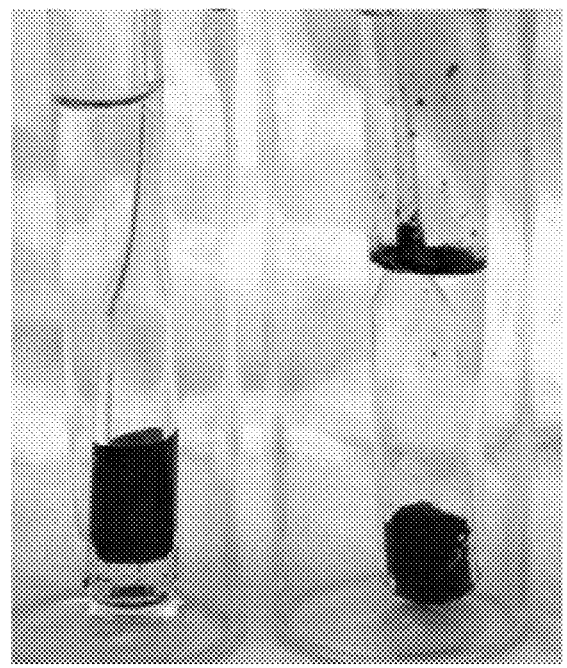

FIG. 1: Microsand Column Oil Release Assay for AL9:8 after: A) 7 days and B) 3 months.

FIG. 2: Profile of the signature sequences in bacterial 16S rDNA variable regions 3 (2A) and 6 (2B) for *Thauera* sp AL9.8, developed from an alignment of the partial its 16S rDNA sequence with other published 16S rDNA sequences of *Thauera* species in the GenBank sequence database using *Azoarcus* sp BH72 full length gene as the alignment anchor.

FIG. 3: Alignment of ebdA-like protein sequence of *Thauera* sp AL9.8 with ebdA protein sequence from strain *Azoarcus* sp. EbN1 ebdA1 protein sequence. Score=973 bits (2514), Expect=0.0; Identities=463/521 (88%), Positives=494/521 (94%) (the same or similar aa residues), Frame=+1, +=aa residue substitution with an aa of similar charge and hydrophobicity properties, ●=aa residue substitution with an aa of different charge and hydrophobicity properties FIG. 4: Formation of a hydrophobic biofilm structure.

Figure 5:
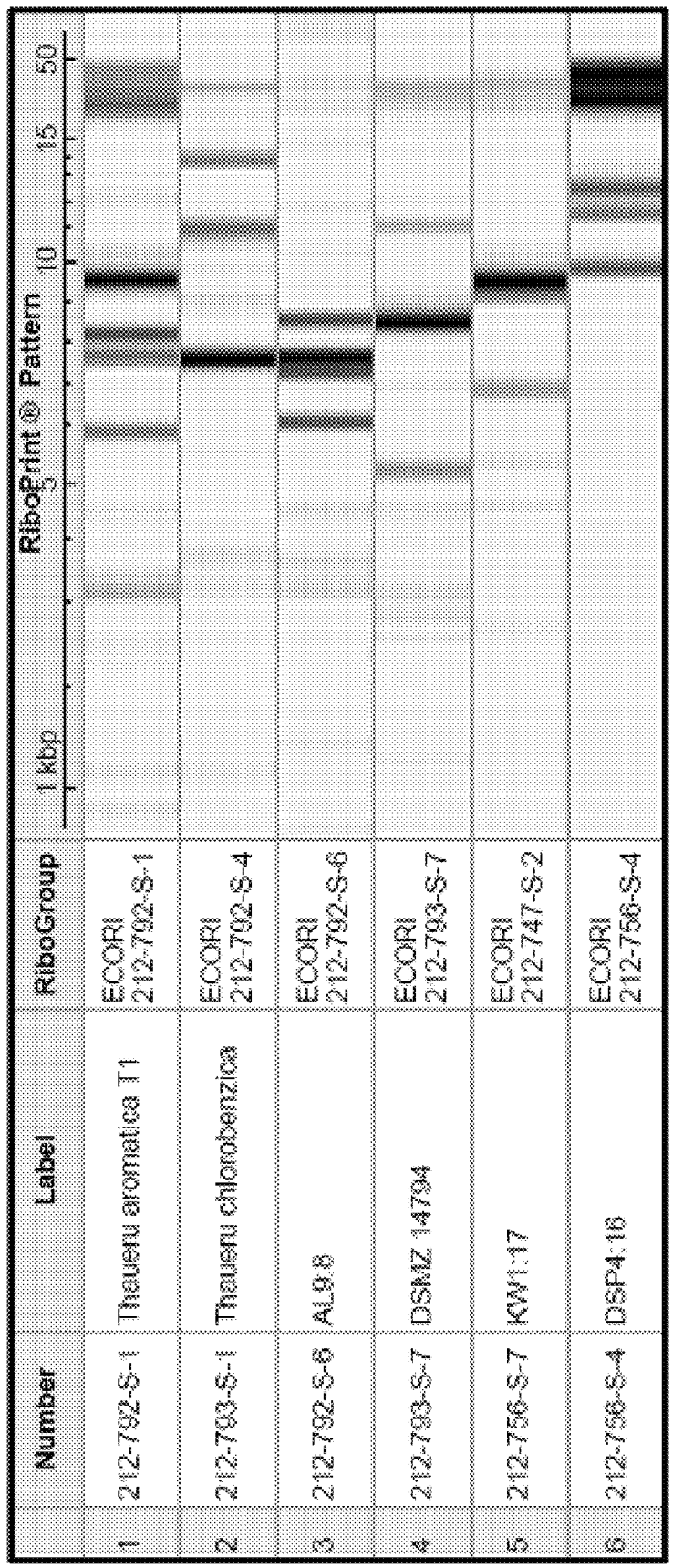

FIG. 5: Riboprint data produced for *Thauera* AL9:8 and selected, closely related strains of *Thauera* (*T. aromatica* T1, *Thaera chlorobenzica*, AL9:8, DSMZ 14794) and *Azoarcus* (KW1:17), and a distant strain of *Pseudomonas stutzeri* (DSP4:16).

The following sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST .25 (1998) and the sequence listing requirements of the EPO and PCT (Rules 5.2 and 49.5 (a-bis)), and Section 208 and Annex C of the Administrative Instructions. The symbols and format used for nucleotide and amino acid sequence data comply with the rules set forth in 37 C.F.R. §1.822.

TABLE 1

PRIMER SEQUENCES USED IN THIS INVENTION

| Description | SEQ ID NO: Nucleic acid |
|---|---|
| 8F forward primer | 1 |
| 1492 R reverse primer | 2 |
| 1407 R reverse primer | 3 |
| bssA-1369F forward primer | 13 |
| bssA-1429R reverse primer | 14 |
| bcr-Ebn1-175F forward primer | 15 |
| bcr-Ebn1-286R reverse primer | 16 |
| ebdA-EbN1-956F forward primer | 17 |
| ebdA-EbN1-1038R reverse primer | 18 |
| ebdA-793F FWD | 21 |
| ebdA-793 REV | 22 |
| ebdA-617F FWD | 23 |
| ebdA-617R REV | 24 |
| ebdA-516F FWD | 25 |
| ebdA-516R REV | 26 |
| ebdA-879F FWD | 27 |
| ebdA-879R REV | 28 |
| ebdA-895-fwd | 36 |
| ebdA-973-rev | 37 |
| ebdA-926-T | 38 |
| 16S-1369-fwd | 39 |
| 16S-1389-T | 40 |

TABLE 2

List of SEQ ID Numbers of Expression Genes and Proteins

| Description | SEQ ID NO: |
|---|---|
| *Thauera* sp. strain AL9.8, partial 16S rDNA | 4 |
| *Thauera* sp. strain AL9.8, 16S rDNA variable region 3 signature sequence - base no. 335-386 | 5 |
| *Thauera* sp. strain AL9.8, 16S rDNA variable region 6 signature sequence - base no. 995-1034 | 6 |
| AY945908 Uncultured bacteria Clone DR-7 (*Thauera* sp.), 16S rDNA | 7 |
| *Thauera aromatica* (Strain LG356), 16S rDNA | 8 |
| *Thauera aromatica* (Strain S100), 16S rDNA | 9 |
| *Thauera* sp. (Mz1T) 16S rDNA | 10 |
| *Thauera* sp. (T1) 16S rDNA GENE | 11 |
| *Azoarcus* sp. (BH72), 16s rDNA | 12 |
| 83 bp amplified partial ebdA-like gene DNA sequence | 19 |
| 41 bp amplified partial ebdA-like gene DNA sequence internal to ebdA_EbN1 primers_emb|CR555306.1 | 20 |
| Partial ebd-like gene *Thauera* strain AL9:8, 1564 bp | 29 |
| *Azoarcus* sp., ebdA gene sequence (EbN1 complete genome) | 30 |
| *Azoarcus* sp., EB1, ethylbenzene dehydrogenase gb|AF337952 | 31 |
| *Thauera* sp. AL9:8 partial ebdA protein sequence from | 32 |
| *Azoarcus* sp. EbN1, ethylbenzene dehydrogenase, alpha subunit protein sequence (YP_160313.1) | 33 |

TABLE 2-continued

List of SEQ ID Numbers of Expression Genes and Proteins

| Description | SEQ ID NO: |
|---|---|
| *Azoarcus* sp. EbN1, ethylbenzene dehydrogenase, alpha subunit protein sequence (YP_158333.1) | 34 |
| *Azoarcus* sp. EB1, ethylbenzene dehydrogenase subunit A protein sequence | 35 |

TABLE 3

INFORMATION ON DEPOSITED STRAIN

| Depositor Identification Reference | International Depository Designation | Date of Deposit |
|---|---|---|
| *Thauera* sp. strain AL9.8 | ATCC No. PTA-XXX | Sep. XX, 2008 |

DETAILED DESCRIPTION OF THE INVENTION

The invention relates to the identification of a previously unknown microorganism obtained from an environmental site, which had been exposed to tar, creosol and polycyclic aromatic hydrocarbons (PAHs). Enrichment cultures were developed as microcosms of microbes that would grow on crude oil under denitrifying conditions. A screening protocol was then developed to isolate and identify pure microbe strains capable of growth under denitrifying conditions using oil or oil components as the sole source of carbon. These microbes could be grown in situ in an oil reservoir for enhancement of oil recovery. The present invention provides two amplified sequences, a partial 16S rDNA sequence (SEQ ID NO:4) and a partial ebdA-like gene sequences (SEQ ID NOs:29) that genetically identify the present bacterial strain. This microorganism is further defined by its riboprint pattern as presented in Example 7 of this application.

The following definitions are provided for the special terms and abbreviations used in this application:

The abbreviation "dNTPs" refers to Deoxyribonucleotide triphosphates. The term "ddNTPs" refer to deoxynucleotides that lack, in addition to their 2'-OH group, the 3'-OH group on their deoxyribose sugar.

The abbreviation "ATCC" refers to American Type Culture Collection International Depository, Manassas, Va., USA. "ATCC No." refers to the accession number to cultures on deposit with ATCC.

The abbreviation "ASTM" refers to the American Society for Testing and Materials.

The term "environmental sample" means any sample exposed to hydrocarbons, including a mixture of water and oil. As used herein environmental samples include water and oil samples that comprise indigenous microorganisms useful for phylogenetic mapping of genera present in a given sampling area.

The term "enrichment culture" or "microcosm" may be used herein interchangeably and refer to a culture of organisms grown in a medium of known composition and under specific conditions of incubation that favor the growth of particular types of microorganisms (Bacteria or Archaea), e.g.; growing organisms in a denitrifying medium using oil as the sole carbon source.

The terms "oil well" and "oil reservoir" may be used herein interchangeably and refer to a subterranean or sea-bed formation from which oil may be recovered.

The term "improving oil recovery" refers to the process of using hydrocarbon-utilizing microorganisms, which are endemic in petroleum reservoirs, where they occur naturally using hydrocarbons as a food source to alter physico-chemical properties of the reservoir/crude oil. As a result of this process, hydrocarbon-utilizing microorganisms can change the physico-chemical properties of the crude oil through excretion of bio-products such as alcohols, gases, acids, surfactants and polymers. Changed physico-chemical properties are, e.g., those described under the term "modifying the environment of oil well", infra.

The term "growing on oil" means the microbial species are capable of metabolizing hydrocarbons or other organic components of crude petroleum as a nutrient to support growth.

The term "electron acceptor" refers to a chemical entity that accepts electrons transferred to it from another compound. It is an oxidizing agent that, by virtue of its accepting electrons, is itself reduced in the process.

The terms "denitrifying" and "denitrification" mean reducing nitrate for use in respiratory energy generation.

The term "sweep efficiency" means the ability of injected water to 'push' oil through a geological formation toward a producer well. One problem that can be encountered with waterflooding operations is the relatively poor sweep efficiency of the water, i.e., the water can channel through certain portions of the reservoir as it travels from the injection well(s) to the production well(s), thereby bypassing other portions of the reservoir. Poor sweep efficiency may be due, for example, to differences in the mobility of the water versus that of the oil, and permeability variations within the reservoir which encourage flow through some portions of the reservoir and not others.

The term "pure culture" means a culture derived from a single cell isolate of a microbial species. The pure cultures specifically referred to herein include those that are publicly available in a depository. Additional pure cultures are identifiable by the methods described herein.

The term "biofilm" means a film or "biomass layer" of microorganisms. Biofilms are often embedded in extracellular polymers, which adhere to surfaces submerged in, or subjected to, aquatic environments.

The terms "simple nitrates" and "simple nitrites" refer to nitrite ($NO_2$) and nitrate ($NO_3$).

The term "modifying the environment of oil well" may include one or more of the following processes 1) altering the permeability distribution of the subterranean formation (sweep efficiency), (2) producing biosurfactants which decrease surface and interfacial tensions, (3) alter the properties of the rock in the reservoir as to make the surface more wetted with water than oil and thereby releasing oil from the rock surface, (4) producing polymers that increase the viscosity of the water and thus improve the ability of the thicker water to move oil from the pore space of the rock; (5) generating gases (predominantly $CO_2$) that increase formation pressure; and (6) reducing oil viscosity.

The abbreviation "NCBI" refers to the National Center for Biotechnology Information.

The term "ribotyping" means fingerprinting of genomic DNA restriction fragments that contain all or part of the genes coding for the 16S and 23S rRNA.

The term "ribotyping profile" means the specific fingerprint of genomic DNA restriction fragments that contain all or substantially of the genes coding for the 16S and 23S rRNA obtained for a strain. FIG. 5, row 3 represents the ribotyping profile for AL9:8.

The term "microbial species" means distinct microorganisms identified based on their physiology, morphology and phylogenetic characteristics using 16S rDNA sequences.

The abbreviation "rDNA" refers to Ribosomal Deoxyribonucleic Acid.

The term "rDNA typing" means the process of utilizing the sequence of the gene coding for 16S rDNA to obtain the "closest relative" microbial species by homology to rDNA sequences maintained in several international databases. The closest relative microbial species may also be referred to as a "homolog".

"Real-time polymerase chain reaction" or "quantitative real time polymerase chain reaction (q-PCR)", is a laboratory technique based on the polymerase chain reaction, to amplify and simultaneously quantify a targeted DNA molecule. It enables both detection and quantification (as absolute number of copies or relative amount when normalized to DNA input or additional normalizing genes) of a specific sequence in a DNA sample.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to: the GCG suite of programs (Wisconsin Package Version 9.0, Genetics Computer Group (GCG), Madison, Wis.), BLASTP, BLASTN, BLASTX (Altschul et al., *J. Mol. Biol.* 215, 403-410, 1990), DNASTAR (DNASTAR, Inc., Madison, Wis.), and the FASTA program incorporating the Smith-Waterman algorithm (Pearson, W. R., *Comput. Methods Genome Res.*, Proc. Int. Symp, Meeting Date 1992, 111-120, Eds: Suhai, Sandor, Plenum Publishing, New York, N.Y., 1994). Within the context of this application, it will be understood that, where sequence analysis software is used for analysis, the results of the analysis will be based on the "default values" of the program referenced, unless otherwise specified. As used herein "default values" will mean any set of values or parameters which originally load with the software when first initialized.

Additional abbreviations used in this application are as follows: "hr" means hour(s), "min" means minute(s), "mL" means milliliters, "mg/mL" means milligram per milliliter, "L" means liters, "µL" means microliters, "mM" means millimolar, "µM" means micromolar, "nM" means nano molar, "µg/L" means microgram per liter, "° C." means degrees Centigrade or Celsius, "bp" means base pair(s), "mm" means millimeter, "ppm" means part per million, "g/L" means gram per liter, "ng/µL" means nanogram per microliter, "cfu/mL" means colony forming units per milliliter, "g" means gram, "mg/L" means milligram per liter, "LB" means Luria broth, "rpm" means revolution per minute, and "%" means percent, "v/v" means volume for volume, "v/v/v" means volume for volume for volume, "sec" means second(s), "%" means percent, "g" is the gravitational unit.

The invention relates to the isolation and identification of a previously unknown soil microorganism obtained from an environmental site, which had been exposed to tar, creosol and polycyclic aromatic hydrocarbons (PAHs). The soil samples were taken from an anaerobic zone, 6-8 feet below the surface. The samples were used to inoculate enrichment cultures to enrich for a consortium of microbes for their use of crude oil as the sole carbon source under denitrifying conditions. This was followed by an isolation and screening protocol developed to isolate and identify the microbes capable of growth under denitrifying conditions using oil or oil components as their sole source of carbon. The microbe of the present invention could be grown in situ in an oil reservoir for the enhancement of oil recovery.

Within the context of the present invention, applicants have outlined the signature regions within *Thauera* strain AL9:8's 16S rDNA (SEQ ID NO: 4) that are defined in SEQ ID NO:5 (within the prokaryote 16s rRNA variable region 3) and SEQ ID NO: 6 (within the prokaryote 16s rRNA variable region 6). These sequence variable regions were discovered when the 16S rDNA sequence profile of *Thauera* sp. AL9.8 was aligned with other published 16S rDNA sequences from *Thauera* sp. (SEQ ID NO:7 through 12) in the database using *Azoarcus* sp. BH72 full 16S sequence (SEQ ID NO:12) as the alignment anchor. FIG. 2A shows signature base variations occur in the 16S variable region 3 SEQ ID NO: 5 at specific coordinate positions: A336, A347, A372 and A377 and are observed across various *Thauera* and *Azoarcus* strains. Concomitantly, a similar observation is made for bacterial variable region 6 for sequences closely related to *Thauera* strain AL9:8 e.g., sequences similar to that defined by SEQ ID NO: 6 can be found in published sequences. Strain variations occur at positions, A999, A1012 and A1033 as shown in FIG. 2B. These signature bases are diagnostic to the identification of *Thauera* sp. including *Thauera* strain AL9:8. There are two *Thauera* 16S rDNA-like sequence, which are found in sequence databases, that contain the diagnostic sequences within variable region 3 that are similar to those defined by SEQ ID NO: 5 and SEQ ID NO: 6. These are uncultured bacterium clone DR7 (NCBI GenBank accession No. gb|AY945908.1|) and *Thauera* strain LG356 (NCBI, EMBL Accession No. emb|AJ315680.1|).

The presence of the ebdA-like partial protein sequence contained within SEQ ID NO: 32, which has 88% identities= (463/521) and 94% positives (494/521), further defines *Thauera* strain AL9:8 and distinguishes it from the other *Thauera* strains that may contain similar 16S sequences. The 1564 bp's sequence obtained of an ebdA-like gene (DNA) sequence for *Thauera* strain AL9:8 is identified in (SEQ ID NO:29). Base sequences between coordinates 40 and 1564 show 84% identities (1356/1543) and 2% gaps (36/1543) in the nucleotide sequence with an expect value of 0.

Riboprint analysis performed on strain AL9:8 chromosomal rRNA genetic elements offers an additional level of genetic identification for this unique strain and directly differentiates this strain from its closest relatives at the 16S rDNA sequence level. Riboprint analysis is able to resolve the differences that exist in chromosomal structure with respect to genes for the small and large rRNA subunits, e.g., 5S, 16S, 23S.

The present disclosure thus provides a method for identifying a bacterium containing the signature genetic sequences set forth above. These diagnostic sequences were generated by PCR amplification of the DNA of a bacterium capable of using oil or oil components, under denitrifying conditions, as its sole carbon source.

Bioremediation and Oil Pipeline Maintenance

The ability of *Thauera* strain AL9:8 to metabolize hydrocarbons makes this strain useful in the bioremediation of areas contaminated with hydrocarbons. Thus, also provided herein are methods for decontaminating or remediating contaminated areas by applying to the area(s) bacterial isolate *Thauera* strain AL9:8, which is then allowed to metabolize or mobilize the contaminants in situ. Bioremediation takes place when *Thauera* strain AL9:8 cells are exposed to hydrocarbons and convert them into products such as carbon dioxide, water, and oxygen or when growth of the *Thauera* strain AL9:8 cells allow release of high molecular weight hydrocarbons to the surface for subsequent removal by physical clean up methods. In some embodiments, *Thauera* strain AL9:8 can be incubated in the environment to be bioremediated without any added co-substrate, or other carbon or energy source. The bioremediation process can be monitored by periodically taking samples of the contaminated environment, extracting the hydrocarbons, and analyzing the extract using methods known to one skilled in the art.

Contaminated substrates that may be treated with *Thauera* strain AL9:8 include, but are not limited to, beach sand, harbor dredge spoils, sediments, wastewater, sea water, soil, sand, sludge, air, and refinery wastes. In another embodiment, the contaminated substrate can be an oil pipeline. Hydrocarbon incrustation and sludge buildup are significant causes of decreased pipeline performance and can eventually lead to failure of the pipeline. Because of the ability of *Thauera* strain AL9:8 to release hydrocarbons, its application to an oil pipeline containing incrusted hydrocarbons or hydrocarbon-containing sludge can be useful in the removal of the unwanted hydrocarbons from the pipeline.

In some embodiments, other agents effective in the bioremediation of hydrocarbons can be added to a *Thauera* strain AL9:8 bioremediation composition. These other agents may include a microorganism or more than one microorganism, such as a bacterium, a yeast, or a fungus. The agents may also include a chemical compound that is not lethal to *Thauera* strain AL9:8, but is effective at degrading or partially degrading hydrocarbons and/or other contaminants or stimulating growth of this strain to affect oil release. Microorganisms may be delivered to the contaminated substrate by any one of the many well known methods including those described by Newcombe, D. A., and D. E. Crowley (Appl. Microbiol. Biotechnol., (1999), 51:877-82); Barbeau, C., et al., (Appl. Microbiol. Biotechnol., (1997), 48:745-52); and U.S. Pat. Nos. 6,573,087, 6,087,155, and 5,877,014.

Screening for Hydrophobicity

There is a direct correlation between cell surface hydrophobicity and (bio)surfactant production in many hydrocarbon-associated microbes. Surfactant production by microorganisms can act to stabilize desired oil water emulsions for improved sweep efficiency of produced fluids in oil reservoirs. While biosurfactant production is one means by which microorganisms stabilize emulsions, some are capable of stabilizing emulsions in the absence of active cell growth and presumably biosurfactant production. This suggests that the cell surface properties of a microorganism may act to stabilize emulsions of oil/water interface via general hydrophobic interactions of cell surfaces with the oil/water interface. (Dorobantu Loredana S. et al., Appl. Environ. Biol., (2004), 70:6333-6336). The method used in this invention to access cell surface hydrophobicity is a modification of a procedure which indirectly measures hydrophobicity through the attachment of microbes to polystyrene plates (Pruthi, V. and Cameotra, S., Biotechnol. Techniques, (1997), 11: 671-674). In this assay a drop of the culture of the microbes was placed on a microscope slide and covered with a coverslip. The hydrophobic strain adheres to the surface of the coverslip and can be detected using dark field microscopy, that allows visualization of bacteria by scattered light by using a specialized disc in the condenser that blocks greater than 90% light from passing though the specimen.

Screening strains for emulsification of hexadecane—Microorganisms synthesize a wide variety of biosurfactants and bio-emulsifiers that lower surface and interfacial tensions and produce stable emulsions. An emulsification test was developed based on a modification of the BATH test (Pruthi and Cameotra, supra). Aliquots (500 µL) of the bacterial cultures were mixed with 500 µL hexadecane in a sealed vial and agitated for 1 min at high speed using a Vortex mixer and hexadecane emulsification was monitored over time. Cultures that produced emulsions that lasted longer than 30 min were considered positive for biosurfactant or bio-emulsifier production.

General Methods

Growth of Microorganisms

Techniques for growth and maintenance of anaerobic cultures are described in "Isolation of Biotechnological Organisms from Nature", (Labeda, D. P. ed. 117-140, McGraw-Hill Publishers, 1990). For denitrification, anaerobic growth is measured by nitrate depletion from the growth medium over time. Nitrate is utilized as the primary electron acceptor under the growth conditions used herein. The reduction of nitrate to nitrogen has been previously described (Moreno-Vivian, C., et al., J. Bacteriol., (1999), 181: 6573-6584). In some cases nitrate reduction processes lead to nitrite accumulation which is subsequently further reduced to nitrogen. Accumulation of nitrite is therefore also considered evidence for active growth and metabolism by microorganisms. Depletion of nitrite is also evidence of growth and metabolism by microorganisms.

Ion Chromatography

To quantitate nitrate and nitrite ions in aqueous media, Applicants used an ICS2000 chromatography unit (Dionex, Banockburn, Ill.) equipped with an AS15 anion exchange column and a gradient of 2 to 50 mM potassium hydroxide. Standard curves using known amounts of sodium nitrite or sodium nitrate solutions were generated and used for calibrating nitrate and nitrite concentrations.

Screening to Discover Environmental Isolates Capable of Growth on Oil Components A screening protocol to discover novel pure cultures capable of growth on and/or modification of petroleum components was implemented as follows:

Environmental soil samples were obtained from an environmental site, which had been exposed to tar, creosol and polycyclic aromatic hydrocarbons (PAHs). Soil samples were taken from pits dug 6 feet below the surface where PAHs have been shown to be at elevated levels. A soil sample was diluted (at 1 to 10 w/v ratio) and incubated with the minimal salts medium for 72 hr. A 1-to-10-dilution of this sample was then used as an inoculum for the minimal salts medium, supplemented with 300 ppm nitrate and autoclaved crude oil (1:2 ratio of oil phase to aqueous phase; 15 mL of autoclaved crude oil to 30 mL of SL10 medium (Table 1) as the sole carbon source.

Enrichment/Screening Protocol

Once growth was recorded in the original enrichment cultures, a series of enrichment subcultures were propagated using the primary enrichment cultures as inocula and crude oil as the sole carbon source. The ratio of the oil to aqueous phase was 1:2. These subcultures will be referred to as parent cultures. Microbial growth of parent cultures was accomplished in 60 mL serum vials that contained 30 mL of the minimal salts medium, with 1.6 g/L sodium nitrate (Table 1) and 10.0 mL autoclaved crude oil. Inoculation was done in an anaerobic glove bag and cultures were maintained anaerobically in sealed vials. These cultures were grown with moderate shaking (100 rpm) at ambient temperatures for weeks to months and examined regularly for nitrate depletion and nitrite accumulation and depletion. When all available nitrate was reduced, the parent culture was either subcultured to a fresh medium plus substrate vial or supplemented with additional sodium nitrate, (250-2000 ppm). After several months of growth and 1 to 3 sub-culturing steps, the resulting subcultures were serially diluted and streaked onto 1.5% agar LB or R2A medium plates (Teknova, Hollister, Calif., USA) with or without NaNO$_3$ (500 ppm) to obtain isolated single colonies of the various culturable strains. The plates were incubated at ambient temperature either anaerobically (with NaNO$_3$) or aerobically (without NaNO$_3$ added) until colonies were formed. Colonies having various morphologies were selected, transferred to fresh plates for further growth, and then distributed into 50 µL of sterile deionized water for direct genomic rDNA sequencing analysis.

Direct Colony rDNA Sequence Analysis

Genomic DNA from bacterial colonies was isolated by diluting bacterial colonies in 50 µL of water or Tris-HCL buffer pH7-8. Diluted colony DNAs were amplified with Phi 29 DNA polymerase prior to sequencing (GenomiPHI Amplification Kit GE Life Sciences, New Brunswick, N.J.). An aliquot (1.0 µL) of the diluted colony was added to 9.0 µL of the Lysis Reagent (from the GenomiPHI Amplification Kit) and heated to 95° C. for 3.0 min followed by immediate cooling to 4° C. 9.0 µL of Enzyme Buffer and 1.0 µL of Phi 29 enzyme were added to each lysed sample followed by incubation at 30° C. for 18 hr. The polymerase was inactivated by heating to 65° C. for 10 min followed by cooling to 4° C.

DNA sequencing reactions were set up as follows: 8.0 µL of GenomiPHI amplified sample were added to 8.0 µL of BigDye v3.1 Sequencing reagent (Applied Biosystems, Foster City, Calif.) followed by 3.0 µL of 10 µM primers SEQ ID NO: 1 in combination with SEQ ID NO: 2 or NO: 3 (prepared by Sigma Genosys, Woodlands, Tex.), 4.0 µL of 5× BigDye Dilution buffer (Applied Biosystems) and 17 µL Molecular Biology Grade water (Mediatech, Inc., Herndon, Va.).

Sequencing reactions were heated for 3.0 min at 96° C. followed by 200 thermocycles of (95° C. for 30 sec; 55° C. for 20 sec; 60° C. for 2 min) and stored at 4° C. Unincorporated fluorescently labeled ddNTPs were removed using Edge Biosystems (Gaithersburg, Md.) clean-up plates. Amplified reactions were pipetted into one well of a pre-spun 96 well clean up plate. The plate was centrifuged for 5.0 min at 5,000× g in a Sorvall RT-7 (Sorvall, Newtown, Conn.) at 25° C. The cleaned up reactions were placed directly onto an Applied Biosystems 3730 DNA sequencer and sequenced with automatic basecalling.

Each of the assembled rDNA sequences was compared to the NCBI rDNA database (~260,000 rDNA sequences) using the BLAST algorithm (Altschul et al., supra). The primary hit was used as an identifier of the most closely related known species identification. The initial screen using the rDNA colony direct sequencing reduced the number of colonies to be carried through further screening by 20 fold. The unique isolate set was then used to screen for growth on oil as a sole carbon source under denitrifying conditions.

Extraction of Genomic DNA from Bacterial Cultures

To extract genomic DNA from liquid bacterial cultures, cells were harvested by centrifugation (10,000 rpm, at room temperature) and resuspended in the following lysis buffer (100 mM Tris-HCL, 50 mM NaCl, 50 mM EDTA, pH8.0) followed by agitation using a Vortex mixer. The following reagents were then added to a final concentration of 2.0 mg/mL lysozyme, 10 mg/mL SDS, and 10 mg/mL Sarkosyl to lyse the cells. After further mixing with a Vortex mixer, 0.1 mg/mL RNAse and 0.1 mg/mL Proteinase K were added to remove the RNA and protein contaminants and the mixture was incubated at 37° C. for 1.0-2.0 hr.

Post incubation, the samples were extracted twice with an equal volume of a phenol: chloroform: isoamyl alcohol (25: 24:1, v/v/v) and once with chloroform: isoamyl alcohol (24: 1). One-tenth volume of 5.0M NaCl and two volumes of 100% ethanol were added to the aqueous layer, and mixed. The tubes were frozen at −20° C. overnight and then centrifuged at 15,000×g for 30 min at room temperature to pellet chromosomal DNA. The pellets were washed once with 70% ethanol, centrifuged at 15,000×g for 10 min, dried, resuspended in 100 µL of de-ionized water and stored at −20° C. An aliquot of the extracted DNA was visualized on an agarose gel to ascertain the quantity and quality of the extracted DNA.

Real Time Quantitative PCR (q-PCR) Assay Design

Gene-Specific Primers and TagMan Pobes were designed based on sequence information using Primer Express software (Applied Biosystems, Foster City, Calif.). Primers were synthesized by MWG-Biotech Inc. (High Point, N.C.), and TagMan MGB probes with fluorophore FAM or TAMRA labels at the 5' end and a non-fluorescent quencher at the 3' end were synthesized by Applied Biosystems (Foster City, Calif.). During the combined annealing/extension phase of PCR, the probe is cleaved by the 5' to 3' exonuclease activity of the Taq DNA polymerase, releasing the florophore in the reaction (Holland et al., 1991). This results in a detectable 'quantitiy' of FAM that is proportional to the amount of accumulated PCR product. The point at which the fluorescent signal reaches a significant level above background is recorded as the Ct or 'threshold cycle' value for each PCR reaction. The Ct values inversely correlate to target copy number. The slope of the log dilution vs Ct values can be used to evaluate PCR efficiency versus an expected value of 1.0=100% efficiency.

Microsand Column Oil Release Test

Isolated bacterial strains were examined for their ability to release oil from sand using a microsand column assay to visualize oil release. The microsand column consisted of an inverted glass Pasteur pipette containing produced sand (10 to 100 microns) from the Alaskan North Slope oil reservoirs, which has been coated with crude oil and allowed to age for at least one week. Specifically, oil and sand were autoclaved separately, transferred to a vacuum oven, dried at 180° C. for a minimum of one week and combined (~1:1 v/v) in an anaerobic environment. The mixtures were stirred and allowed to age for a minimum of seven days in an anaerobic environment. The barrels of glass Pasteur pipette (5.75") were cut to approximately half height (3") and autoclaved. The cut end of the pipette was plunged into the sand/oil mix and the core filled to about 0.5 inches in height from the bottom of the pipette barrel. The cut end of the pipette containing the oil/ sand mixture was placed (with the tapered end of the pipette pointing upward) into the 13 mm glass test tube and a test inoculum in ~4.0 mL of minimal salts medium was added to the 13 mm glass tube. The apparatus was sealed inside a glass vial (23×95 mm) in an anaerobic environment. Oil released from the sand is collected in the narrow neck of the Pasteur pipettes or as droplets on the surface of the sand layer. Cultures that enhanced release of oil over background (sterile medium) were presumed to have altered the interaction of the oil with the sand surface, demonstrating the potential to contribute to enhancing oil recovery in a petroleum reservoir.

Automated Ribotyping

Automated ribotyping was used for conclusive identification of selected strains with similar 16S rDNA sequence phylogenetic characteristics (Webster, John A, 1988. U.S. Pat. No. 4,717,653; Bruce, J. L., Food Techno., (1996), 50: 77-81; and Sethi, M. R., Am. Lab. (1997), 5: 31-35). Ribotyping was performed as recommended by the manufacturer (DuPont Qualicon Inc., Wilmington, Del.). For these analyses, one fresh colony was picked, resuspended in the sample buffer and added to the processing module for the heat treatment step at 80° C. for 10 min to inhibit endogenous DNA-degrading enzymes. The temperature was then reduced and lytic enzymes lysostaphin and N-acetyl-muramidase, provided by the manufacturer, were added to the sample. The sample carrier was then loaded onto the Riboprinter system with other commercial reagents. Restriction enzyme digestion using EcoRI enzyme, gel electrophoresis and blotting steps were completely automated. Briefly, bacterial DNA was digested with the EcoRI restriction enzyme and loaded onto an agarose gel: restriction fragments were separated by electrophoresis and then transferred to a nylon membrane. After a denaturation step, the nucleic acids were hybridized with a sulfonated DNA probe containing the genes for the small and large rRNA subunits of E. coli, the 5S, 16S, 23S and ribosomal rRNAs. The hybridized labeled-probe was detected by capturing light emission from a chemiluminescent substrate with a charge-coupled device camera. The output consisted of a densitometry finger scan depicting the specific distribution of the EcoRI restriction fragments containing the genomic rDNA sequences and their molecular weights, which are particular to the genomic DNA sequence of a specific strain independent of the 16S rDNA sequence.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Characterization of Bacterial Isolates Grown Anaerobically on Oil as the Sole Carbon Source Representatives of unique colony morphologies isolated from long-term enrichment cultures growing on oil were used as the inoculum in subsequent growth studies using crude oil as the sole carbon source. Isolated colonies were screened by PCR amplification using the direct colony rDNA analysis described in the General Methods and the combination of forward and reverse primers, SEQ ID NO:1 and SEQ ID NO:2 or NO:3, followed by sequencing of their 16S rDNA. The rDNA sequence from each colony was aligned and matched with the GenBank sequence database for phylogenetic strain identification. Purified isolates of each unique strain were inoculated under anaerobic conditions into 20 mL serum vials containing a 1:2 ratio of minimal salts medium to autoclaved crude oil: 10 mL minimal salts medium (Table 4), 0.4 g/L sodium nitrate with 5.0 mL of autoclaved crude oil. The medium was deoxygenated by sparging the filled vials with a mixture of nitrogen and carbon dioxide followed by autoclaving. All manipulations of bacteria were done in an anaerobic chamber (Coy Laboratories Products, Inc., Grass Lake, Mich.). These cultures were incubated at ambient temperatures for several weeks to several months and monitored for nitrate and nitrite levels, for visible turbidity and or for visible changes to the integrity of the oil phase. When nitrate was depleted in any culture, aliquots of sodium nitrate (50 g/L stock solution) were added to increase its concentration in the medium to 0.4 to 1.6 g/L.

TABLE 4

Minimal Salts Medium

| Growth component | Final Concentration | Chemical Source |
|---|---|---|
| Nitrogen | 18.7 µM | $NH_4Cl$ |
| Phosphorus | 3.7 µM | $KH_2PO_4$ |
| Magnesium | 984 µM | $MgCl_2 \cdot 6H_2O$ |
| Calcium | 680 µM | $CaCL_2 \cdot 2H_2O$ |
| Sodium chloride/ | 172 mM | NaCl |
| Sodium iodide | 1% | NaI |
| Trace metals | 670 µM | nitrilotriacetic acid |
|  | 15.1 µM | $FeCl_2 \cdot 4H_2O$ |
|  | 1.2 µM | $CuCl_2 \cdot 2H_2O$ |
|  | 5.1 µM | $MnCL_2 \cdot 4H_2O$ |
|  | 12.6 µM | $CoCl_2 \cdot 6H_2O$ |
|  | 7.3 µM | $ZnCl_2$ |
|  | 1.6 µM | $H_3BO_3$ |
|  | 0.4 µM | $Na_2MoO_4 \cdot 2H_2O$ |
|  | 7.6 µM | $NiCl_2 \cdot 6H_2O$ |
| Selenium-tungstate | 22.8 nM | $Na_2SeO_3 \cdot 5H_2O$ |
|  | 24.3 nM | $Na_2WO_4 \cdot 2H_2O$ |
| pH buffer/Bicarbonate | 23.8 nM | $NaHCO_3$ |
| vitamins | 100 µg/L | vitamin B12 |
|  | 80 µg/L | p-aminobenzoic acid |
|  | 20 µg/L | nicotinic acid |
|  | 100 µg/L | calcium pantothenate |
|  | 300 µg/L | pyridoxine hydrochloride |
|  | 200 µg/L | thiamine-HCL $\cdot 2H_2O$ |
|  | 50 µg/L | alpha-lipoic acid |
| Electron acceptor | 0.4 g/L | $NaNO_3$ |

The pH of the medium was adjusted to between 7.4-7.8.

Table 5 shows the results of these growth studies. Pure cultures, which showed growth through nitrate reduction and increased turbidity with oil as the sole carbon substrate, were chosen as "capable of growth on oil under denitrifying conditions". Two isolates designated "strain AL9.8" and "strain AL9:5" grew on oil as the sole source of carbon and depleted 100% of the nitrate within 30 days (Table 5). Both of these isolates were matched by 16S rDNA sequences similarity to the published 16S rDNA sequences for an uncultured bacterium, designated clone DR7 (NCBI GenBank accession No. gb|AY945908.1|), and Thauera strain LG356 (NCBI, EMBL Accession No. emb|AJ315680.1|). Since both isolates performed similarly, strain AL9:8 was chosen for further studies. A single colony of this isolate was inoculated into the medium salts containing sodium nitrate at 0.4 g/L.

TABLE 5

Nitrate Reduction as a Measure of Anaerobic Growth with Oil as the Sole Carbon Source

| Bacteria isolate | 16S Genus ID | % nitrate reduction Soil | time (months) |
|---|---|---|---|
| AL9:0 (NIC[1]) | n.a. | 0 | 1 |
| AL9:1 | Pseudomonas sp. | 0 | 1 |
| AL9:2 | Pseudomonas sp. | 0 | 1 |
| AL9:3 | Pseudomonas sp. | 0 | 1 |
| AL9:4 | Pseudomonas sp. | 0 | 1 |
| AL9:5 | Thauera sp. | 100 | 1 |
| AL9:6 | Pseudomonas sp. | 0 | 1 |
| AL9:7 | Azoarcus sp. | 0 | 1 |
| AL9:8 | Thauera sp. | 100 | 1 |

[1]NIC: Non inoculated control

Example 2

Screening of Single Colony Bacterial Isolate for Enhanced Oil Release

Microsand Column

The isolated bacterial strain *Thauera* strain AL9:8 was examined for its ability to release oil from sand in a visual oil release assay using the microsand column described above. Inocula from *Thauera* strain AL9:8 was grown in the minimal salts medium listed in Table 4 using sterilized crude oil as the carbon source until turbidity was observed. The cell density of each species was measured at $OD_{550}$. All operations for preparation of the microsand columns, inoculation and growth were done in an anaerobic chamber using sterile techniques. The microsand columns (filled with oil-saturated sand as previously described) were placed in each glass tube, with the tapered neck of the Pasteur pipettes pointing up. A four mL aliquot of the inoculum was added to the 13 mm glass tubes either directly or diluted 2:2 to a final 4.0 mL volume with minimal salts medium. The outer vials were sealed in the anaerobic chamber and allowed to incubate at ambient temperatures for the next several weeks. Each column was periodically checked for oil release. Cultures that enhanced release of oil over background (sterile medium) were presumed to have altered the interaction of the oil with the sand surface.

Oil release from the sand is visualized by the released oil collecting in the tapered neck of the Pasteur pipettes or forming droplets on the surface of the sand layer (FIG. 1). Oil release was observed for *Thauera* strain AL9:8 only 3 hr after inoculation. Microsand columns were then observed over the course of several weeks. A slight increase in the amount of oil released was observed after 3 months of incubation. Uninoculated controls did not show visual release of oil over the course of the experiment. Triton® X-100 (Rohm & Haas Co registered trade mark); a nonionic surfactant was used as a positive assay for the release of oil from sand. Table 6 lists the enrichment cultures tested and the observations of oil release after 7 days and 3 months incubation at ambient temperatures.

TABLE 6

Release of Oil from Microsand Columns

| Inoculum ID | Dilution | Oil release: T = _7 days | Oil release: T = _3 months |
|---|---|---|---|
| Controls | | | |
| 1.0% Triton | no | +++ | ++++ |
| 1.0% Triton | ½ | ++ | +++ |
| NIC (medium) | no | − | − |
| Thauera strain | | | |
| AL9:8 | no | + | ++ |
| AL9:8 | ½ | − | + |

1. Microsand columns were scored for oil release on a scale of 1-5 (+) in order of increased oil release; (−) = no release of oil, 5 = complete release of oil from oil coated sand. T = time A second set of microsand columns were set up as above using combined inocula that were grown from the following purified strains: *Thauera* strain AL9:8, *Pseudomonas* strain LH4:15 and *Shewanella* strain LH4:18 to determine whether there was a synergistic effect of these combined inocula on oil release. Each strain was aerobically grown in a Modified Luria Broth (MLB) medium which is composed of a standard LB medium formulation purchased form Mediatech Inc. (Herndon, Va.) with the following additions: sodium phosphate buffer, $MgSO_4$, trace metals, and vitamin (see MLB medium supplements, Table 7) at 30° C. until turbidity was observed. A final concentration of cfu/mL for each strain was determined by plating selected aliquots of serially diluted culture. A final concentration of $1.2 \times 10^8$ cfu/mL was determined for *Thauera* strain AL9:8 after 72 hr incubation at 30° C. LH4:15 and LH4:18 cultures were grown after 16 hr to an approximate concentration of $3.3 \times 10^9$ cfu/mL and $7.8 \times 10^9$ cfu/mL respectively. The cell density of each species was also measured at $OD_{550}$. Strain AL9:8, was then diluted 1:5 in each of two diluents preparations: 1) SL10 minimal salts medium (Table 4) that had been supplemented with sodium acetate (1.0 g/L), sodium succinate (2.0 g/L) and yeast extract (2.0 g/L); or diluent 2: minimal salts medium with out added carbon or yeast extract. Both diluents contained 1000 mg/L $NO_3$ as the electron acceptor. Strains LH4:15 and LH4:18 were diluted 100 fold in the same diluents. The microsand columns (filled with oil-saturated sand as described above) had been placed in each glass tube with the tapered neck of the Pasteur pipettes pointing up and a total aliquot (4.0 mL) of mixed inoculums was added to the 13 mm glass tubes. The diluted inoculum for each regimen described above was then applied to each column set up at approximately a 2:2 v/v ratio (*Thauera* strain AL9:8: LH4:15 or LH4:18) or a 2:1:1 v/v ratio (AL9:8: LH4:15:LH4:18) onto the column set up. All operations for preparation of the microsand columns, inoculation and subsequent incubation were done in an anaerobic chamber using sterile techniques. The outer vials were sealed in the anaerobic chamber and allowed to incubate at ambient temperatures for several weeks. Each column was periodically checked for oil release. Cultures that showed release of oil over background (sterile medium) were presumed to have altered the interaction of the oil with the sand surface. As shown in Table 8, there is an improvement in the release of oil from microsand columns when strain AL9:8 is combined and incubated with strains LH4:15 and or LH4:18.

TABLE 7

MLB medium supplements

| | | |
|---|---|---|
| Trace metals | 670 µM | nitrilotriacetic acid |
| | 15.1 µM | $FeCl_2 \cdot 4H_2O$ |
| | 1.2 µM | $CuCl_2 \cdot 2H_2O$ |
| | 5.1 µM | $MnCL_2 \cdot 4H_2O$ |
| | 12.6 µM | $CoCl_2 \cdot 6H_2O$ |
| | 7.3 µM | $ZnCl_2$ |
| | 1.6 µM | $H_3BO_3$ |
| | 0.4 µM | $Na_2MoO_4 \cdot 2H_2O$ |
| | 7.6 µM | $NiCl_2 \cdot 6H_2O$ |
| $MgSO_4 \cdot 7H_2O$ | 1 g/L | $MgSO_4 \cdot 7H_2O$ |
| E2 vitamins | 100 µg/L | vitamin B12 |
| | 80 µg/L | p-aminobenzoic acid |
| | 20 µg/L | nicotinic acid |
| | 100 µg/L | calcium pantothenate |
| | 300 µg/L | pyridoxine hydrochloride |
| | 200 µg/L | thiamine-HCL•$2H_2O$ |
| | 50 µg/L | alpha-lipoic acid |
| pH buffer/Sodium phosphate | 50 mM | 14 mM $NaH_2PO4$ |
| pH 7.0 | | 36 mM $Na_2HpO4$ |

TABLE 8

Release of oil from Microsand Columns; Mixed inocula - using SL10 medium

| Inoculum ID | Inoculum ratios | Oil release: T = _1 days | Oil release: T = _21 days |
|---|---|---|---|
| NIC (medium) | | – | – |
| NIC (medium) | | – | – |
| AL9:8 | 1 | +/– | + |
| AL9:8 | 1 | – | – |
| AL9:8 + LH4:15 | 1:1 | +/– | ++ |
| AL9:8 + LH4:15 | 1:1 | +/– | + |
| AL9:8 + LH4:18 | 1:1 | + | ++ |
| AL9:8 + LH4:18 | 1:1 | + | +++ |
| AL9:8 + LH4:15 + LH4:18 | 2:1:1 | +/– | + |
| AL9:8 + LH4:15 + LH4:18 | 2:1:1 | +/– | ++ |

Microsand columns were scored for oil release on a scale of 1-5 (+) in order of increased oil release; (–) = no release of oil, 5 = complete release of oil from oil coated sand.

Example 3

Identification of Genes Sequences Involved in Anaerobic Oxidation of Aromatic Compounds and Hydrocarbons The genomic DNA of several purified strains belonging to either the *Thauera* or *Azoarcus* genera was screened for the presence of bssA, bcrA and ebdA genetic elements known to be involved in the anaerobic catabolism of mono-aromatic compounds. To assay for bssA, bcrA, and ebdA genes, genomic DNA was prepared from *Thauera* strain AL9:8, other isolated *Thauera* strains and an isolated *Azoarcus* strain, which had all demonstrated capability of growth using crude oil as their sole carbon source under anaerobic denitrifying conditions. The cells were concentrated from 10 mL of three-day-old cultures grown in modified R2A liquid medium (Table 9) containing 0.4 g/L $NaNO_3$. An aliquot of extracted DNA was electrophoresed on a 0.8% agarose gel in order to ascertain the quantity and quality of extracted DNA. Genomic DNA thus obtained from all strains was then subjected to PCR 16S rDNA typing analysis to verify its origin before using it in bssA, bcrA, and ebdA PCR assays as described below.

TABLE 9

Modified R2A Liquid Medium Formulation

| Growth component | Chemical source | Final concentration |
|---|---|---|
| Vitamins & Growth Factors | Yeast Extract | 0.5 g/L |
| Nitrogen | Proteose Peptone | 0.5 g/L |
| Nitrogen | Casamino Acids | 0.5 g/L |
| Carbon & Energy | Dextrose | 0.5 g/L |
| Carbon & Energy | Sodium Pyruvate | 0.3 g/L |
| Stabilizer | Soluble Starch | 0.5 g/L |
| Phosphorus | $KH_2PO_4$ | 3.7 g/L |
| Magnesium | $MgSO_4 \cdot 7H_2O$ | 0.1 g/L |
| Sodium chloride | NaCl | 1.2 g/L |
| pH buffer (7.5 final) | $Na_2HPO_4 \cdot 7H_2O$ | 0.57 g/L |

The pH of the medium was adjusted to between 7.4-7.8.

PCR Parameters for bssA, bcrA, and ebdA Sequence Amplification

Primers for generating PCR amplicons for the bssA, bcrA, and ebdA genes were designed using Primer Express Software version 2.0 software (Applied Biosystems, Foster City Calif.) to *Thauera aromatica* strain T-1 (bssA gene) and to *Azoarcus* EbN1 for bcrA and ebdA gene sequences as described by Beller et al., (Environ. Sci Technol., (2002), 36: 3977-3984). Primers SEQ ID NO:13 & SEQ ID NO:14, SEQ ID NO:15 & SEQ ID NO:16, SEQ ID NO:17 & SEQ ID NO:18 were designed to amplify a 123 by fragment of the bssA gene, a 112-bp fragment of the bcrA gene, and an 83-bp fragment of the ebdA gene respectively. In this Example, the following isolated strains: *Thauera* strains, AL 2:1, AL 2:5, and AL 9:8 and *Azoarcus* strains, AL 9:7, KW1:18 and KW1:19 were tested by PCR methods for amplification of the bssA, bcrA and ebdA genes using the primer sets listed above. The PCR mix for bssA, bcrA and ebdA amplifications were used in the following procedure: 10 min at 95° C. followed by 40 cycles of: 0:15 min at 95° C., 1:00 min at 60° C., followed by 4° C. hold in a Perkin Elmer GenAmp® System 9700 thermal-cycler (Waltham, Mass.). Resultant amplification products were visualized on 2 and 4% agarose gels (e-gels) from Invitrogen (Carlsbad, Calif.). The bcrA gene was detected in *Thauera* strains AL9:8, AL 2:1 and AL 2:5 and *Azoarcus* strain AL9:7. In addition, an ebdA-like gene sequence was also detected in *Thauera* strain AL9.8. This constitutes a hitherto unreported finding for the *Thauera* genus and underscores the novel genetic structure of *Thauera* strain AL9:8. Table 10 summarizes the results obtained from PCR amplification.

TABLE 10

Confirmation of the presence of bcrA, bssA, ebdA genes in the strains following PCR Amplifications

| strain | Genus | 16S | bssA | bcrA | ebdA |
|---|---|---|---|---|---|
| AL 2:1 | *Thauera* | + | n.t.[1] | + | – |
| AL 2:5 | *Thauera* | + | n.t. | + | – |
| AL 9:7 | *Azoarcus* | + | n.t. | + | – |
| AL 9:8 | *Thauera* | + | + | + | + |
| KW 1:18 | *Azoarcus* | + | + | + | – |
| KW 1:19 | *Azoarcus* | + | + | + | – |

[1]a '+' indicates that amplicons of the correct size were generated for the above gene primer sets, while no DNA controls were negative;
[3]n.t. indicates that the given PCR reaction was not performed on these strains.

The amplification of an ebdA-like gene sequence in *Thauera* strain AL9:8 is a novel finding for the *Thauera* genus. Putative ebdA-like gene sequences were amplified from *Thauera* strain AL9:8 as above and then purified either directly from the PCR reaction using Qiagen PCR Clean Up Kit (Valencia, Calif.) or gel purified from a 4.0% agarose gel using the Quiagen Gel Extraction Kit (Valencia, Calif.) following manufacturer's instructions. The purified ebdA PCR fragment was sequenced either directly and/or cloned into the TOPO TA Cloning Vector from Invitrogen Co. (Carlsbad, Calif.) following manufacturer's protocols. The cloned ebdA-like fragment was subsequently sequenced using an Applied Biosystems 3730 DNA sequencer, and then analyzed with automatic base-calling software.

Sequence results obtained from ebdA-like PCR generated fragment were then blasted against the NCBI database. Both the 83 by PCR fragment in its entirety (SEQ ID NO: 19) and the 41 by sequence obtained, which was internal to the *Azoarcus* EbN1 primer sequence, was used to generate the fragment (SEQ ID NO:20) were blasted. The *Thauera* ebdA-like sequence obtained which is internal to *Azoarcus* EbN1 primers, SEQ ID NO: 20, is underlined below. The top nucleotide hits to both blasted ebdA sequence generated from *Thauera* strain AL9:8 was to the genomic sequence of *Azoarcus* sp., EbN1 (EMBL Accession No. CR555306.1), Table 9. There were 7 nucleotide base changes observed within the 83 by amplified AL9:8 ebdA-like fragment relative to published ebdA sequence for *Azoarcus* strain EbN1.

[SEQ ID NO:19 partial ebdA-like gene sequence from strain AL9:8 (83 bp)].

AGCTCATCGACCGGCAATT<u>CGTCAGC-GAACAGACCGACCTGCCGCTGCTGGTGCGCACGG ATAACGGGAAGTTCCTTAGTGCG</u>

TABLE 11

NCBI Blast Results Obtained for ebdA Purified PCR Fragments 83 bp and 41 bp in Length

| Query Sequence | NCBI Blast Hit | % Identity | Overlap | E Value |
|---|---|---|---|---|
| SEQ ID NO: 19 | emb|CR555306.1*Azoarcus* sp. EbN1 complete genome SEQ. ID NO: 30 | 91% | 76/83 | 6e−26 |
| SEQ ID NO: 20 | emb|CR555306.1*Azoarcus* sp. EbN1 complete genome SEQ. ID NO: 30 | 87% | 24/41 | .002 |

Additional sequence was subsequently obtained from this locus by designing sequencing primers (SEQ NOs: 21-28) to walk out from the 83 bp presumptive ebdA-like sequence obtained above. A 1564 by consensus 'ebdA-like' sequence (SEQ NO:29) was produced from replicate *Thauera* AL9:8 clones whose identity had been confirmed by 16S rDNA sequence analysis. Discrepancies in by mismatches originating from the *Azoarcus* EbN1 primer set initially used to assay for the presence of ebdA in *Thauera* strain AL9:8 were also corrected. The consensus nucleotide sequence listed in SEQ ID NO: 29 was then blasted against the NCBI nucleotide database. Blast results are shown in Table 12. The top two hits to the blasted consensus sequence obtained were to the ebdA gene sequenced from *Azoarcus* strain EbN1 genome (EMBL Accession No. CR555306.1) (SEQ.ID NO:30) and to *Azoarcus* strain EB1's Ethylbenzene dehydrogenase, alpha subunit A (GENBANK Accession No. AF337952) (SEQ.ID NO:31).

TABLE 12

NCBI Blast Results Obtained for 1564 BP Partial ebdA-like Locus for *Thauera* strain AL9:8

| Query Sequence | NCBI Blast Hit | % Identity | Overlap |
|---|---|---|---|
| SEQ ID NO: 29 | emb|CR555306.1*Azoarcus* sp. EbN1 complete genome SEQ. ID NO: 30 | 84% | 1356/1543 |
| SEQ ID NO: 29 | gb|AF337952.1|AF337952 *Azoarcus* sp. EB1 ethylbenzene dehydrogenase SEQ. ID NO: 31 | 84% | 245/290 |

The above nucleic acid sequence was then blasted against the Genpept "nr" dataset, which incorporates non-redundant entries from all Genbank nucleotide translations along with protein sequences from SWISS-PROT protein dataset using blastX. The top 3 protein hits were to *Azoarcus* sp. EbN1 ethylbenzene dehydrogenase and to *Azoarcus* sp. EB1 ethylbenzene dehydrogenase subunitA with an expect value of zero verifying the identity of this sequence as an ethylbenzene like protein present in *Thauera* strain AL9:8. The ebdA protein sequence for *Thauera* strain AL9:8 and its alignment to *Azoarcus* sp. EbN1 ethylbenzene dehydrogenase are included in SEQ.ID NO: 35 and FIG. NO. 3, respectively.

TABLE 13

NCBI BLASTX Protein Results Obtained for 1564 BP Partial ebdA Locus *Thauera* strain AL9:8

| Query Sequence | NCBI BlastX Hit | % Identity | % Similarity | E value |
|---|---|---|---|---|
| SEQ ID NO: 29 | gi|56478724|ref|YP_160313.1| ethylbenzene dehydrogenase, alpha subunit [*Azoarcus* sp. EbN1] SEQ. ID NO: 33 | 88% | 94% | 0 |
| SEQ ID NO: 29 | gi|56476744|ref|YP 158333.1| alpha-subunit of ethylbenzene dehydrogenase [*Azoarcus* sp. EbN1] SEQ. ID NO: 34 | 76% | 87% | 0 |
| SEQ ID NO: 29 | gi|14994027|gb|AAK76387.1| AF337952 1 ethylbenzene dehydrogenase subunit A [*Azoarcus* sp. EB1] SEQ. ID NO: 35 | 75% | 87% | 0 |

Real time q-PCR EbdA Gene-Specific Primers SEQ ID NO: 36, SEQ ID NO.:37) and a TaqMan Minor Groove-Binder (TaqMan MGB) Probe (SEQ ID NO.: 38) were then designed from the additional gene sequence obtained for the *Thauera* strain AL9:8 ebdA locus. Purified genomic DNA's for *Azoarcus* strains 1:18, 1:19, and *Thauera* strain AL9:8 were prepared and DNA concentrations were determined using the Nanoprop ND 1000 spectrophotometer (Thermo Fisher Scientific, Waltham, Mass. 02454). DNA's were diluted to 1 ng/µL then serially diluted 1:10 six additional times, all seven DNA concentrations for each strain as well as a water (no DNA) blank were evaluated with real time PCR primers and probes targeting the ebdA gene and 16S rDNA. Primers were designed using Primer Express v 2.0 software (Applied Biosystems, Foster City, Calif., 94404)

The real time PCR reactions were set up in triplicate as follows: 10 µL TaqMan Universal PCR Mix w/o UNG (#4326614, Applied Biosystems, Foster City, Calif., 94404), 0.2 µL 100 µM ebdA-895-fwd: SEQ ID NO:36, 0.2 µL 100 µM SEQ ID NO.:37 ebdA-973-rev:, and 0.05 µL 100 µM SEQ ID NO.38 or for the 16S q-PCR assay 0.2 µL 100 µM 16S-

1369-fwd: SEQ ID NO.39, 0.2 µL 100 µM 16S-1492-rev SEQ ID NO.2: and 0.05 µL probe, SEQ ID NO.40, 1.0 µL genomic DNA and 8.55 µL molecular biology grade water (MediaTech, Inc, Herndon, Va., 20171). All primers and the 16S probe were obtained from Sigma Genosys, The Woodlands Tex., 77380. The ebdA probe was obtained from Applied Biosystems, Foster City, Calif. 94404.

The real time PCR reactions were thermal cycled on an ABI 7900 SDS instrument (Applied Biosystems, Foster City, Calif., 94404) as follows: 10 min at 95° C. followed by 40 cycles of 95° C. 15 sec+60° C. 1:00 min. During thermal cycling the 7900 SDS collected fluorescence signal data for the reporter dye 6-FAM. Reactions containing the targeted sequence generate fluorescence while those without target do not. The point at which the fluorescent signal reaches a significant level above background is recorded as the Ct or 'threshold cycle' value for each PCR reaction. The Ct values inversely correlate to target copy number. The slope of the log dilution versus Ct values can be used to evaluate PCR efficiency versus an expected value of 1.0=100% (ABI 7700 User Bulletin No 2, Foster City Calif. 94404).

The results in the Table 14 below represent average Ct values for triplicate reactions for *Thauera* strain AL9:8. The results show that the ebdA gene was detected in *Thauera* strain AL9:8. Both the ebdA and the 16S rDNA response to dilution for *Thauera* strain AL9:8 in this assay are within the normal range expected for 100% PCR efficiency.

TABLE 14

Real Time PCR Detection of ebdA in *Thauera* strain AL9:8

| Sample Name | 16S Ct | ebdA Ct | Log Dilution |
|---|---|---|---|
| AL9:8-1 | 20.55 | 21.68 | 0 |
| AL9:8-2 | 24.17 | 25.23 | −1 |
| AL9:8-3 | 27.74 | 28.56 | −2 |
| AL9:8-4 | 31.31 | 31.89 | −3 |
| AL9:8-5 | 34.50 | 35.32 | −4 |
| AL9:8-6 | 37.14 | 38.09 | −5 |
| AL9:8-7 | 31.17 | ND | −6 |

Example 4

Anaerobic Growth of *Thauera* Strain AL9:8'S on Toluene and Ethylbenzene

As demonstrated in the previous examples *Thauera* strain AL9:8 grows in cultures with crude oil as its sole carbon source and contains genetic elements that are known to be involved in the anaerobic degradation of aromatic hydrocarbons that are known natural constituents of crude oil. To further characterize the substrate specificity of *Thauera* strain AL9:8 it was inoculated, under anaerobic conditions, into 60 mL serum vials containing a 1:2 ratio of minimal salts medium to sterilized organic layer containing either toluene or ethylbenzene that had been filter sterilized through PTFE filters and resuspended in autoclaved carrier 2,2,4,4,6,8,8-heptamethylnonane (HMN). Toluene and ethylbenzene organic layers served as the sole carbon source for inoculated vials containing: 30 mL minimal salts medium (Table 4), ~700-800 ppm sodium nitrate with 10.0 mL of a 0.8% and 1.7% toluene or ethylbenzene solution in a HMN carrier. The medium was deoxygenated by sparging the filled vials with a mixture of nitrogen and carbon dioxide followed by autoclaving. All manipulations of bacteria were done in an anaerobic chamber (Coy Laboratories Products, Inc. Grass Lake, Mich.). These cultures were incubated at ambient temperatures for several weeks and monitored for growth by either visible turbidity, optical density ($OD_{550}$) and/or nitrate and nitrite levels. Anaerobic Growth was observed for strain AL9:8 on toluene but not on ethylbenzene to date (Table 15).

TABLE 15

*Thauera* strain AL9:8 Anaerobic Growth on Toluene and Ethylbenzene

| Bacteria isolate | 16S Genus ID | Growth on Toluene | | Growth on Ethylbenzene | |
|---|---|---|---|---|---|
| | | $OD^1$ | $NO_3/NO_2^2$ | $OD^1$ | $NO_3/NO_2^2$ |
| AL9:8 | *Thauera* sp. | + | + | − | − |
| KW1:18 | *Azoarcus* sp. | + | + | − | − |
| KW1:19 | *Azoarcus* sp. | + | + | − | − |

[1] a + indicates an increase in OD,
[2] a + decrease in $NO_3$ levels and or increase in $NO_2$ levels.

Example 5

Demonstrating Hydrophobisity of *Thauera* Strain AL9:8 Cell Surfaces

The method used in this invention was a modification of a procedure which indirectly measures hydrophobicity through the attachment of microbes to polystyrene plates (Pruthi, V. and Cameotra, S., Biotechnol. Techniques, (1997), 11: 671-674). In this assay a drop of the culture of the microbes was placed on a microscope slide and covered with a coverslip. The hydrophobic strain adheres to the surface of the coverslip and can be detected using a microscope. *Thauera* strain AL9.8 was grown to an approximate $OD_{600}$ of 1.0 in 20 mL minimal salts medium (Table 4), containing oil as the sole carbon source. Aliquots (10 µL) of cultures were placed on a microscope slide, covered with a glass coverslip and incubated at room temperature for 2 min. Samples were examined with a Zeiss Axioskop 40 microscope (Carl Zeiss Micro Imaging, Inc, Thornwood, N.Y.), using dark field at 400× magnification. *Thauera* strain AL9:8 cells, grown in the presence of oil, stuck to the glass slide and the cover slip demonstrating a positive hydrophobic response. *Thauera* strain AL9:8 cells grown in the absence of oil did not stick to the glass cover slip and slide.

Example 6

Emulsification of Hexadecane by *Thauera* Strain 9.8

Aliquots (500 µL) of a bacterial cultures that had been grown in a modified DNB medium purchased from Geo-Microbial Technologies (Ochelata, Okla.) were mixed with 500 µL hexadecane in a sealed vial and agitated for 1:00 min at high speed using a Vortex mixer and hexadecane emulsification was monitored over time. Cultures that produced emulsions that lasted longer than 30 min were considered positive for biosurfactants or bio-emulsifiers production.

*Thauera* strain AL9.8 behaved differently in this assay and did not produce a stable emulsion following the 30 min incubation. However when the emulsification test for this strain was continued in 50% hexadecane overnight and then agitated, as described above, an indefinitely stable emulsion was produced. The minimal salts medium control (Table 4), which did not receive an inoculum, did not form an emulsion when mixed even when incubated overnight. These results indicated that presence of a hydrocarbon, such as hexadecane, was required for strain AL9.8 to produce the biosurfactant(s) or bio-emulsifier(s).

Example 7

Formation of a Hydrophobic Biofilm Mass on the Aqueous-Oil Interface by *Thauera* Strain AL9.8

Figure 4A:

*Thauera* strain AL9.8 was grown under anaerobic conditions in 20 mL serum vials containing 10 mL minimal salts medium (Table 4) and 0.4 g/L sodium nitrate with 5.0 mL of autoclaved crude oil at a ratio of 1:2 (v/v) minimal salts medium to autoclaved crude oil. The medium was deoxygenated by sparging the filled vials with a mixture of nitrogen and carbon dioxide followed by autoclaving. All manipulations of bacteria were done in an anaerobic chamber (Coy Laboratories Products, Inc. Grass Lake, Mich.). Following incubation at room temperature (20-25° C.) without shaking for three to four weeks, *Thauera* strain AL9.8 grew as a "biofilm-like" mat at the interface as shown in FIG. 4A. Using a one mL syringe, equipped with a 21-gauge hypodermic needle, an aliquot (50 µL) of this culture was removed from the area close to the oil-aqueous phase interface and a 2.0 µL of this sample was placed on a microscope slide and covered with a 20 mm-square No. 1 coverslip. Samples were examined with a Zeiss Axioskop 40 (Carl Zeiss Micro Imaging, Inc, Thornwood, N.Y.) using a phase imaging microscopy under an oil emersion lens, (1000× magnification).

Figures 4B, 4C, 4D:
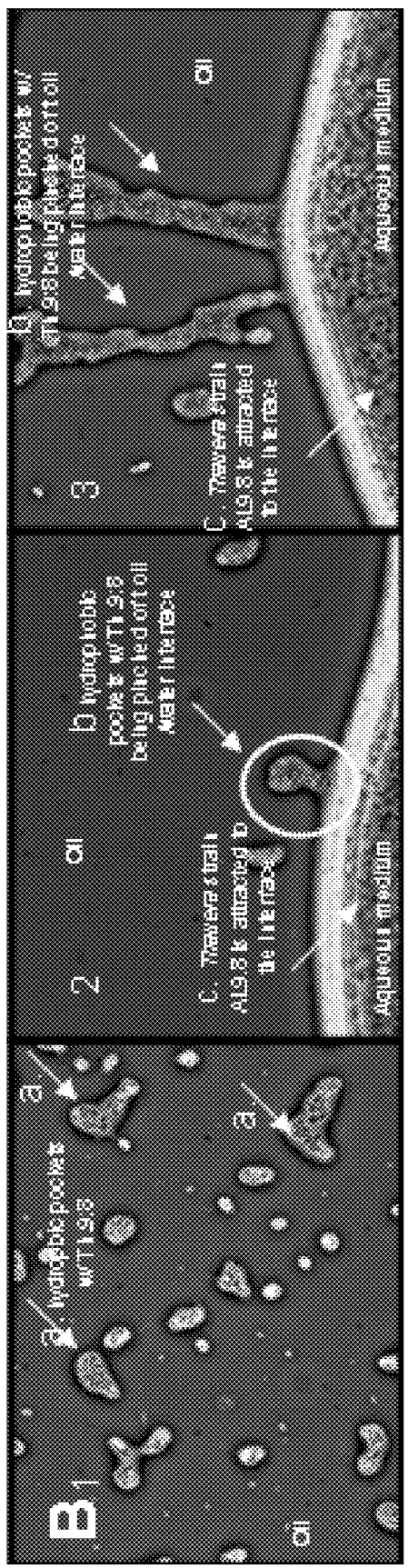
Figures 4E, 4F:
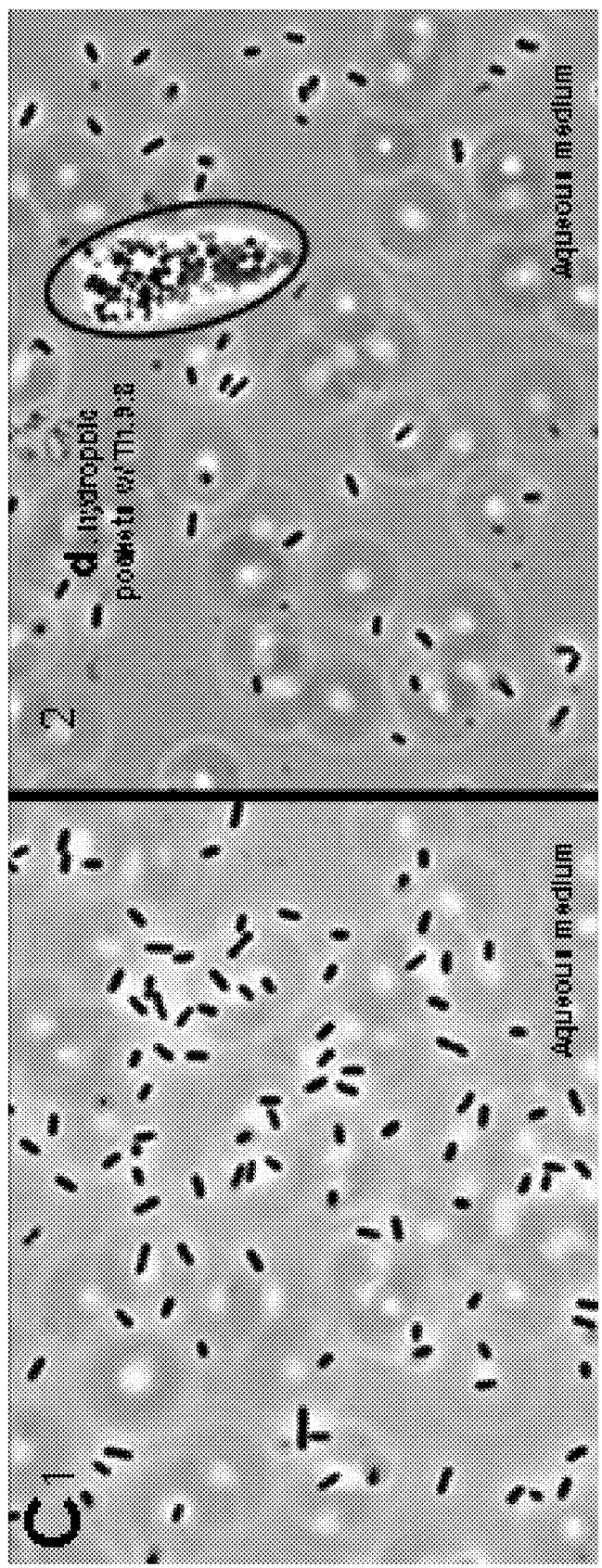

*Thauera* strain AL9.8 was found in the oil phase in irregular "pockets" formed around aggregated bacteria (FIG. 4B1). Normally water droplets, trapped in oil, will produce round droplets. In FIGS. 4B2 and 4B3, it appears that as the aqueous-oil interface has moved toward the bottom of the slide, the bacteria captured at the interface within these aggregated hydrophobic forms (FIG. 4B3) are "pinched-off" and left in the oil phase.

The nature of the formation of *Thauera* strain AL9.8 aggregates at the aqueous-oil interface is also unique. Bacteria are usually attracted to the interface, but stream quickly along the interface in one direction, one bacterium at a time. In this instance, *Thauera* strain AL9.8 is attracted to the interface as a non-motile aggregate mass (FIG. 4B3), along the length of the interface, forming an aggregate of 30 to 50 µm wide.

In the center of the aqueous phase, *Thauera* AL9.8 can be seen as motile cells, not forming aggregates. These cells are not under the influence of the structure formed at the aqueous-oil interface. A few aggregated cell masses (FIG. 4C2) can however be observed randomly within the aqueous phase suggesting that they were probably broken off the hydrophobic biofilm structure when the sample was applied to the microscope slide and covered with a coverslip.

These observations demonstrate formation of a hydrophobic aggregate mass that may contribute to the biofilm formation at the aqueous-oil interface or with an oil/aqueous emulsion. It is assumed that such structure would allow the *Thauera* strain AL9.8 to interact with and use some of the oil components as the sole carbon source for its growth

Example 8

Riboprinting to Confirm Uniqueness of *Thauera* Strain AL9:8

The 16S rDNA sequence of *Thauera* strain AL9:8 was 100% homologous to the 16S rDNA sequences from one previously identified but uncultured *Thauera* strain DR-7 (Liu, B. et al, FEMS Microbiol. Ecol. (2006), 55: 274-286) and one cultured species *Thauera aromatica* LG356 (Mechichi, T. et al. Arch. Microbiol. (2002), 178: 26-35). To verify whether the 16S rDNA from *Thauera* strain AL9:8 contained additional distinguishing elements from its closest neighbors, several preparations of this strain and other selected *Thauera* and *Azoarcus* strains that had been initially isolated from oil enrichment cultures were analyzed by Riboprinter®. *Azoarcus* spp. are members of closely-related genetic cluster of the denitrifying beta-Proteobacteria that degrade alkanes and alkybenzenes. Two *Thauera* strains, *Thauera aromatica* T1 (ATCC 700265) and *Thauera chlorobenzoica* (ATCC 700723), that were 99% homologous to *Thauera* strain AL9:8 16S rDNA sequence, were also used as controls in these analyses. Based on the analyses (FIG. 5), which provide a chromosomal fingerprint of the tested strains, it is clear that the riboprint pattern for *Thauera* strain AL9:8 (lane 3) is unique when compared against 16S rDNA related *Thauera* strains: DSMZ strain 14794, (*Thauera aromatica* LG356) (lane 4), *Thauera aromatica* T1 and *Thauera chlorobenzoica* (lane 1 and 2 respectively). These analyses confirmed that the genomic sequences surrounding the rRNA operon in *Thauera* strain AL9:8 are substantially different from the *Thauera* strains shown in FIG. 5 even though their 16S rDNA sequences are 99%-100% homologous. A strain of *Pseudomonas stutzeri* (lane 6) that shares a sequence homology of 88% to the 16s rDNA sequence of *Thauera* strain AL9:8 is included for comparison. It is possible for various strains to share single similar riboprint bands generated by hybridizing the labeled *E. coli* rDNA operon probe to each strains genomic Eco RI fragments but it is the overall riboprint banding pattern that constitutes identification on a given strain. The riboprint banding pattern occurring between 6 and 10 kB in particular (lane 3:FIG. 5) comprised of one 6 kB band, a doublet running between 7 and 8 kb, with a fourth band running about 8.5 kb is unique to *Thauera* strain AL9:8. The riboprint analysis obtained for *Thauera* strain AL9:8 is further evidence substantiating the uniqueness of *Thauera* strain AL9.8 and further differentiates it from its closest 16S rDNA homologs that have been deposited in public DNA databases.

SEQUENCE LISTING

<160> NUMBER OF SEQ ID NOS: 40

<210> SEQ ID NO 1
<211> LENGTH: 20
<212> TYPE: DNA
<213> ORGANISM: artificial sequence
<220> FEATURE:
<223> OTHER INFORMATION: primer -continued

```
<400> SEQUENCE: 1
agagtttgat ymtggctcag                                                   20

<210> SEQ ID NO 2
<211> LENGTH: 19
<212> TYPE: DNA
<213> ORGANISM: artificial sequence
<220> FEATURE:
<223> OTHER INFORMATION: primer

<400> SEQUENCE: 2
ggwtaccttg ttacgactt                                                    19

<210> SEQ ID NO 3
<211> LENGTH: 35
<212> TYPE: DNA
<213> ORGANISM: artificial sequence
<220> FEATURE:
<223> OTHER INFORMATION: primer

<400> SEQUENCE: 3 gacggggtg wgtrcaagac gggcggtgwg trcaa                                   35

<210> SEQ ID NO 4
<211> LENGTH: 1387
<212> TYPE: DNA
<213> ORGANISM: Thauera sp.

<400> SEQUENCE: 4
agcgggggct tcggcctgcc ggcgagtggc gaacgggtga gtaatgcatc ggaacgtgcc       60
catgtcgtgg gggataacgt atcgaaaggt acgctaatac cgcatacgtc ctgagggaga     120 aagcgggga tcttcggacc tcgcgcgatt ggagcggccg atgtcggatt agctagtagg     180
tgaggtaaag gctcacctag gcgacgatcc gtagcgggtc tgagaggatg atccgccaca     240
ctgggactga gacacggccc agactcctac gggaggcagc agtggggaat tttggacaat     300
gggcgcaagc ctgatccagc catgccgcgt gagtgaagaa ggccttcggg ttgtaaagct     360
ctttcggccg ggaagaaatc gtggtctcta acataggcca tggatgacgg taccggacta     420
agaagcaccg gctaactacg tgccagcagc cgcggtaata cgtagggtgc gagcgttaat     480
cggaattact gggcgtaaag cgtgcgcagg cggttttgta agacagatgt gaaatccccg     540
ggctcaacct gggaactgcg tttgtgactg caaggctaga gtacggcaga gggggtgga     600 attcctggtg tagcagtgaa atgcgtagag atcaggagga acaccgatgg cgaaggcagc     660
cccctgggcc tgtactgacg ctcatgcacg aaagcgtggg gagcaaacag gattagatac     720
cctggtagtc cacgccctaa acgatgtcga ctagtcgttc ggagcagcaa tgcactgagt     780
gacgcagcta acgcgtgaag tcgaccgcct ggggagtacg gccgcaaggt taaaactcaa     840
aggaattgac ggggacccgc acaagcggtg gatgatgtgg attaattcga tgcaacgcga     900
aaaaccttac ctaccttga catgccagga accttgccga gaggcgaggg tgccttcggg     960
agcctggaca caggtgctgc atggctgtcg tcagctcgtg tcgtgagatg ttgggttaag    1020
tcccgcaacg agcgcaaccc ttgtcactag ttgccatcat ttggttgggc actctagtga    1080
gactgccggt gacaaaccgg aggaaggtgg ggatgacgtc aagtcctcat ggcccttatg    1140
ggtagggctt cacacgtcat acaatggtcg gtacagaggg ttgccaagcc gcgaggtgga    1200
gccaatccct taaagccgat cgtagtccgg atcgtagtct gcaactcgac tacgtgaagt    1260
```

```
cggaatcgct agtaatcgca gatcagcatg ctgcggtgaa tacgttcccg ggtcttgtac    1320
acaccgcccg tcacaccatg ggagtgggtt tcaccagaag taggtagctt aaccttcggg    1380
agggcgc                                                              1387

<210> SEQ ID NO 5
<211> LENGTH: 56
<212> TYPE: DNA
<213> ORGANISM: Thauera sp.

<400> SEQUENCE: 5
actcctacgg gaggcagcag tggggaattt tggacaatgg gcgcaagcct gatcca         56

<210> SEQ ID NO 6
<211> LENGTH: 45
<212> TYPE: DNA
<213> ORGANISM: Thauera sp.

<400> SEQUENCE: 6
atgccaggaa ccttgccgag aggcgagggt gccttcggga gcctg                     45

<210> SEQ ID NO 7
<211> LENGTH: 1503
<212> TYPE: DNA
<213> ORGANISM: Thauera sp.

<400> SEQUENCE: 7
gagagtttga tcctggctca gattgaacgc tggcggcatg ctttacacat gcaagtcgaa      60
cggcagcggg ggcttcggcc tgccggcgag tggcgaacgg gtgagtaatg catcggaacg     120
tgcccatgtc gtgggggata acgtatcgaa aggtacgcta ataccgcata cgtcctgagg     180
gagaaagcgg gggatcttcg gacctcgcgc gattggagcg gccgatgtcg gattagctag    240
taggtgaggt aaaggctcac ctaggcgacg atccgtagcg ggtctgagag gatgatccgc    300
cacactggga ctgagacacg gcccagactc ctacgggagg cagcagtggg gaattttgga    360
caatgggcgc aagcctgatc agccatgccg cgtgagtga agaaggcctt cgggttgtaa     420
agctctttcg gccgggaaga atcgtggtc tctaacatag gccatggatg acggtaccgg     480
actaagaagc accggctaac tacgtgccag cagccgcggt aatacgtagg gtgcgagcgt    540
taatcggaat tactgggcgt aaagcgtgcg caggcggttt tgtaagacag atgtgaaatc    600
cccgggctca acctgggaac tgcgtttgtg actgcaaggc tagagtacgg cagaggggg    660 tggaattcct ggtgtagcag tgaaatgcgt agagatcagg aggaacaccg atggcgaagg    720
cagccccctg ggcctgtact gacgctcatg cacgaaagcg tggggagcaa acaggattag    780
ataccctggt agtccacgcc ctaaacgatg tcgactagtc gttcggagca gcaatgcact    840
gagtgacgca gctaacgcgt gaagtcgacc gcctggggag tacggccgca aggttaaaac    900
tcaaaggaat tgacggggac ccgcacaagc ggtggatgat gtggattaat tcgatgcaac    960
gcgaaaaacc ttacctaccc ttgacatgcc aggaaccttg ccgagaggcg agggtgcctt   1020
cgggagcctg gacacaggtg ctgcatggct gtcgtcagct cgtgtcgtga tgttgggt    1080 taagtcccgc aacgagcgca acccttgtca ctagttgcca tcatttggtt gggcactcta    1140
gtgagactgc cggtgacaaa ccggaggaag gtggggatga cgtcaagtcc tcatggccct    1200
tatgggtagg gcttcacacg tcatacaatg gtcggtacag agggttgcca agccgcgagg    1260
tggagccaat cccttaaagc cgatcgtagt ccggatcgta gtctgcaact cgactacgtg    1320
aagtcggaat cgctagtaat cgcagatcag catgctgcgg tgaatacgtt cccgggtctt    1380
```

| | |
|---|---|
| gtacacaccg cccgtcacac catgggagtg ggtttcacca gaagtaggta gcttaacctt | 1440 |
| cgggagggcg cttaccacgg tgagattcat gactggggtg aagtcgtaac aaggtagccg | 1500 |
| tag | 1503 |

<210> SEQ ID NO 8
<211> LENGTH: 1514
<212> TYPE: DNA
<213> ORGANISM: Thauera aromatic

<400> SEQUENCE: 8

| | |
|---|---|
| ctggctcaga ttgaacgctg gcggcatgct ttacacatgc aagtcgaacg gcagcggggg | 60 |
| cttcggcctg ccggcgagtg gcgaacgggt gagtaatgca tcggaacgtg cccatgtcgt | 120 |
| gggggataac gtatcgaaag gtacgctaat accgcatacg tcctgaggga gaaagcgggg | 180 |
| gatcttcgga cctcgcgcga ttggagcggc cgatgtcgga ttagctagta ggtgaggtaa | 240 |
| aggctcacct aggcgacgat ccgtagcggg tctgagagga tgatccgcca cactgggact | 300 |
| gagacacggc ccagactcct acgggaggca gcagtgggga attttggaca atgggcgcaa | 360 |
| gcctgatcca gccatgccgc gtgagtgaag aaggccttcg ggttgtaaag ctctttcggc | 420 |
| cgggaagaaa tcgtggtctc taacataggc catggatgac ggtaccggac taagaagcac | 480 |
| cggctaacta cgtgccagca gccgcggtaa tacgtagggt gcgagcgtta atcggaatta | 540 |
| ctgggcgtaa agcgtgcgca ggcggttttg taagacagat gtgaaatccc cgggctcaac | 600 |
| ctgggaactg cgtttgtgac tgcaaggcta gagtacggca gaggggggtg aattcctgg | 660 |
| tgtagcagtg aaatgcgtag agatcaggag gaacaccgat ggcgaaggca gcccctggg | 720 |
| cctgtactga cgctcatgca cgaaagcgtg gggagcaaac aggattagat accctggtag | 780 |
| tccacgccct aaacgatgtc gactagtcgt tcggagcagc aatgcactga gtgacgcagc | 840 |
| taacgcgtga agtcgaccgc ctggggagta cggccgcaag gttaaaactc aaaggaattg | 900 |
| acggggaccc gcacaagcgg tggatgatgt ggattaattc gatgcaacgc gaaaaacctt | 960 |
| acctacccctt gacatgccag gaaccttgcc gagaggcgag ggtgccttcg ggagcctgga | 1020 |
| cacaggtgct gcatggctgt cgtcagctcg tgtcgtgaga tgttgggtta agtcccgcaa | 1080 |
| cgagcgcaac ccttgtcact agttgccatc atttggttgg gcactctagt gagactgccg | 1140 |
| gtgacaaacc ggaggaaggt ggggatgacg tcaagtcctc atggccctta tgggtagggc | 1200 |
| ttcacacgtc atacaatggt cggtacagag ggttgccaag ccgcgaggtg gagccaatcc | 1260 |
| cttaaagccg atcgtagtcc ggatcgtagt ctgcaactcg actacgtgaa gtcggaatcg | 1320 |
| ctagtaatcg cagatcagca tgctgcggtg aatacgttcc cggtcttgt acacaccgcc | 1380 |
| cgtcacacca tgggagtggg tttcaccaga agtaggtagc ttaaccttcg ggagggcgct | 1440 |
| taccacggtg agattcatga ctggggtgaa gtcgtaacaa ggtagccgta tcggaaggtg | 1500 |
| cggctggatc acct | 1514 |

<210> SEQ ID NO 9
<211> LENGTH: 1501
<212> TYPE: DNA
<213> ORGANISM: Thauera aromatica

<400> SEQUENCE: 9

| | |
|---|---|
| agattgaacg ctggcggcat gctttacaca tgcaagtcga acggcagcgg ggcttcggc | 60 |
| ctgccggcga gtggcgaacg ggtgagtaat gcatcggaac gtgcccatgt cgtgggggat | 120 |

```
aacgtatcga aaggtacgct aataccgcat acgtcctgag ggagaaagcg ggggatcttc      180
ggacctcgcg cgattggagc ggccgatgtc ggattagcta gtaggtgagg taaaggctca      240
cctaggcgac gatccgtagc gggtctgaga ggatgatccg ccacactggg actgagacac      300
ggcccagact cctacgggag gcagcagtgg ggaattttgg acaatggggg caaccctgat      360
ccagccatgc cgcgtgagtg aagaaggcct tcggttgta aagctctttc ggccgggaag       420
aaatcgtggt ctctaacata ggccatggat gacggtaccg gactaagaag caccggctaa      480
ctacgtgcca gcagccgcgg taatacgtag ggtgcgagcg ttaatcggaa ttactgggcg      540
taaagcgtgc gcaggcggtt ttgtaagaca gatgtgaaat ccccgggctc aacctggaa       600 ctgcgtttgt gactgcaagg ctagagtacg gcagaggggg gtggaattcc tggtgtagca      660
gtgaaatgcg tagagatcag gaggaacacc gatggcgaag gcagccccct gggcctgtac      720
tgacgctcat gcacgaaagc gtggggagca acaggatta gataccctgg tagtccacgc       780
cctaaacgat gtcgactagt cgttcggagc agcaatgcac tgagtgacgc agctaacgcg      840
tgaagtcgac cgcctgggga gtacggccgc aaggttaaaa ctcaaaggaa ttgacgggga     900
cccgcacaag cggtggatga tgtggattaa ttcgatgcaa cgcgaaaaac cttacctacc     960
cttgacatgc caggaacctt gctgagaggc gagggtgcct tcgggagcct ggacacaggt    1020
gctgcatggc tgtcgtcagc tcgtgtcgtg agatgttggg ttaagtcccg caacgagcgc    1080 aaccccttgtc actagttgcc atcatttggt tgggcactct agtgagactg ccggtgacaa   1140
accggaggaa ggtggggatg acgtcaagtc ctcatggccc ttatgggtag gcttcacac     1200 gtcatacaat ggtcggtaca gagggttgcc aagccgcgag gtggagccaa tcccaaaaag    1260
ccgatcgtag tccggatcgt agtctgcaac tcgactacgt gaagtcggaa tcgctagtaa    1320
tcgcagatca gcatgctgcg gtgaatacgt tcccgggtct tgtacacacc gcccgtcaca   1380
ccatgggagt gggtttcacc agaagtaggt agcttaacct tcgggagggc gcttaccacg    1440
gtgagattca tgactggggt gaagtcgtaa caaggtagcc gtatcggaag gtgcggctgg    1500
a                                                                   1501

<210> SEQ ID NO 10
<211> LENGTH: 1479
<212> TYPE: DNA
<213> ORGANISM: Thauera sp.
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t

<400> SEQUENCE: 10
tagagtttga tcatggctca gattgaacgc tggcggcatg ctttacacat gcaagtcgaa      60
cggcagcggg ggcttcggcc tgccggcgag tggcgaacgg gtgagtaatg catcggaacg     120
tgcccatgtc gtgggggata acgtagcgaa agctacgcta ataccgcata cgccctgagg    180 ggaaagcgg gggattcttc ggaacctcgc gcgattggag cggccgatgt cggattagct      240
agtangtgag gtaaaggctc acctaggcga cgatccgtag cgggtctgag aggatgatcc    300
gccacactgg gactgagaca cggcccagga ttcctacggg aagcagcagt ggggaatttt    360
ggacaatggg cgcaagcctg atccagccat gccgcgtgag tgaagaaggc cttcggttg     420 taaagctctt tcggccggga agaaatcgtg gtctctaaca taggccatgg atgacggtac    480
```

```
cggactaaga agcaccggct aactacgtgc cagcagccgc ggtaatacgt agggtgcgag    540
cgttaatcgg aatactgggc gtaaagcgtg cgcaggcggt tttgtaagac agatgtgaaa    600
tccccgggct taacctggga actgcgtttg tgactgcaag gctagagtac ggcagagggg    660
ggtggaattc ctggtgtagc agtgaaatgc gtagagatca ggaggaacac cgatggcgaa    720
ggcagccccc tgggcctgta ctgacgctca tgcacgaaag cgtggggagc aaacaggatt    780
aggatacccct ggtagtccac gccctaaacg atgtcgacta gtcgttcgga gcagcaatgc    840
actgagtgac gcagctaacg cgtgaagtcg accgcctggg gagttacggc cgcaaggtta    900
aaactcaaag gaattgacgg ggacccgcac aagcggtgga tgatttggat taattcgatg    960
caacgcgaaa aaccttacct acccttgaca tgtctggaac cttgctgnga ggcgagggtg   1020
ccttcgggag ccagaacaca ggtgctgcat ggctgtcgtc agctcgtgtc gtgagatgtt   1080
gggttaagtc cgcaacgag cgcaacccctt gtcaatagtt gccatcattt ggttgggcac   1140
tctagtgaga ctgccggtga caaaccggag gaaggtgggg atgacgtcaa gtcctcatgg   1200
cccttatggg tagggcttca cacgtcatac aatggtcggt acagagggtt gccaagccgc   1260
gaggtggagc caatcccta aagccgatcg tagtccggat cgtagtctgc aactcgacta   1320
cgtgaagtcg gaatcggtag taatcgcaga tcagcatgct gcggtgaata cgttcccggg   1380
tcttgtacac accgcccgtc acaccatggg agtgggtttc accagaagta ggtagcttaa   1440
ccttcgggga gggcgcttac cacggtgaga ttcatgact                          1479
```

<210> SEQ ID NO 11
<211> LENGTH: 1531
<212> TYPE: DNA
<213> ORGANISM: Thauera sp.

<400> SEQUENCE: 11

```
ttagagtttg atcctggctc agattgaacg ctggcggcat gctttacaca tgcaagtcga     60
acggcagcgg gggcttcggc ctgccggcga gtggcgaacg ggtgagtaat gcatcggaac    120
gtgcccatgt cgtgggggat aacgtatcga aggtacgct aataccgcat acgtcctgag    180
ggagaaagcg ggggatcttc ggacctcgcg cgattggagc ggccgatgtc ggattagcta    240
gtaggtgagg taaaggctca cctaggcgac gatccgtagc gggtctgaga ggatgatccg    300
ccacactggg actgagacac ggcccaactc tacgggaggc agcagtgggg aattttggac    360
aatgggggca accctgatcc agccatgccg cgtgagtgaa gaaggccttc gggttgtaaa    420
gctctttcgg ccgggaagaa atcgtggtct ctaacatagg ccatggatga cggtaccgga    480
ctaaaagcac cggctaacta cgtgccagca gccgcggtaa tacgtagggt gcgagcgtta    540
atcggaatta ctgggcgtaa agcgtgcgca ggcggttttg taagacagat gtgaaatccc    600
cgggctcaac ctgggaactg cgtttgtgac tgcaaggcta gagtacggca gagggggtg    660
gaattcctgg tgtagcagtg aaatgcgtag agatcaggag gaacaccgat ggcgaaggca    720
gccccctggg cctgtactga cgctcatgca cgaaagcgtg gggagcaaac aggattagat    780
accctggtag tccacgccct aaacgatgtc gactagtcgt tcggagcagc aatgcactga    840
gtgacgcagc taacgcgtga agtcgaccgc ctggggagta cggccgcaag gttaaaactc    900
aaaggaattg acggggaccc gcacaagcgg tggatgatgt ggattaattc gatgcaacgc    960
gaaaaacctt acctaccctt gacatgccag gaaccttgct gagaggcgag ggtgccttcg   1020
ggagcctgga cacaggtgct gcatggctgt cgtcagctcg tgtcgtgaga tgttgggtta   1080
```

```
agtcccgcaa cgagcgcaac ccttgtcact agttgccatc atttggttgg gcactctagt    1140
gagactgccg gtgacaaacc ggaggaaggt ggggatgacg tcaagtcctc atggccctta    1200
tgggtagggc ttcacacgtc atacaatggt cggtacagag ggttgccaag ccgcgaggtg    1260
gagccaatcc caaaaagccg atcgtagtcc ggatcgtagt ctgcaactcg actacgtgaa    1320
gtcggaatcg ctagtaatcg cagatcagca tgctgcggtg aatacgttcc cgggtcttgt    1380
acacaccgcc cgtcacacca tgggagtggg tttcaccaga agtaggtagc ttaaccctcg    1440
ggagggcgct taccacggtg agattcatga ctggggtgaa gtcgtaacaa ggtagccgta    1500
tcggaaggtg cggctggatc acctccttaa a                                    1531

<210> SEQ ID NO 12
<211> LENGTH: 1534
<212> TYPE: DNA
<213> ORGANISM: Azoarcus sp.

<400> SEQUENCE: 12
aacttaagag tttgatcctg gctcagattg aacgctggcg gcatgcttta cacatgcaag      60
tcgaacggca gcgggggctt cggcccgccg gcgagtggcg aacgggtgag taatgcatcg     120
gaacgtgccc agtcatgggg gataactacg cgaaagcgta gctaataccg catacgccct     180
gagggggaaa gtggggatc gcaagacctc acgtgattgg agcggccgat gtcagattag     240
ctagttggtg aggtaaaggc tcaccaaggc gacgatctgt agcgggtctg agaggatgat     300
ccgccacact gggactgaga cacggcccag actcctacgg gaggcagcag tggggaattt     360
tggacaatgg gcgaaagcct gatccagcca tgccgcgtga gtgaagaagg ccttcgggtt     420
gtaaagctct ttcggacgga agaaatcgc gcgggctaat atcccgcgtg gatgacggta     480
ccgtaagaag aagcaccggc taactacgtg ccagcagccg cggtaatacg tagggtgcga     540
gcgttaatcg gaattactgg gcgtaaagcg tgcgcaggcg gttttgtaag acaggtgtga     600
aatccccggg cttaacctgg gaactgcgct tgtgactgca aggctagagt acggcagagg     660 gggtggaat ccacgtgta gcagtgaaat gcgtagagat gtggaggaac accgatggcg     720
aaggcagccc cctgggcctg tactgacgct catgcacgaa agcgtgggga gcaaacagga     780 ttagatacccc tggtagtcca cgccctaaac gatgtcaact agttgttcgt agaggtaact     840
ctgtgagtaa cgcagctaac gcgtgaagtt gaccgcctgg ggagtacggc cgcaaggtta     900
aaactcaaag gaattgacgg ggacccgcac aagcggtgga tgatgtggat taattcgatg     960
caacgcgaaa aaccttacct acccttgaca tgcctggaac cttggtgaga gccgagggtg    1020
ccttcgggaa ccaggacaca ggtgctgcat ggctgtcgtc agctcgtgtc gtgagatgtt    1080
gggttaagtc ccgcaacgag cgcaacccctt gtcattaatt gccatcattc agttgggcac    1140
tttaatgaga ctgccggtga caaaccggag gaaggtgggg atgacgtcaa gtcctcatgg    1200
cccttatggg tagggcttca cacgtcatac aatggtcggt acagagggtt gccaaaccgc    1260
gaggtggagc taatccctta aagccgatcg tagtccggat cgtagtctgc aactcgactg    1320
cgtgaagtcg gaatcgctag taatcgcaga tcagcatgct gcggtgaata cgttcccggg    1380
tcttgtacac accgcccgtc acaccatggg agtgggtttc accagaagta ggtagcttaa    1440
ccttcgggag ggcgcttacc acggtgagat tcatgactgg ggtgaagtcg taacaaggta    1500
gccgtatcgg aaggtgcggc tggatcacct cctt                                1534

<210> SEQ ID NO 13
<211> LENGTH: 18
```

```
<212> TYPE: DNA
<213> ORGANISM: artificial sequence
<220> FEATURE:
<223> OTHER INFORMATION: primer

<400> SEQUENCE: 13
acgacggcgg catttctc                                                        18

<210> SEQ ID NO 14
<211> LENGTH: 18
<212> TYPE: DNA
<213> ORGANISM: artificial sequence
<220> FEATURE:
<223> OTHER INFORMATION: primer

<400> SEQUENCE: 14
gcatgatcgg caccgaca                                                        18

<210> SEQ ID NO 15
<211> LENGTH: 23
<212> TYPE: DNA
<213> ORGANISM: artificial sequence
<220> FEATURE:
<223> OTHER INFORMATION: primer

<400> SEQUENCE: 15
gagctctacg gctacaacag cat                                                  23

<210> SEQ ID NO 16
<211> LENGTH: 23
<212> TYPE: DNA
<213> ORGANISM: artificial sequence
<220> FEATURE:
<223> OTHER INFORMATION: primer

<400> SEQUENCE: 16
gagctctacg gctacaacag cat                                                  23

<210> SEQ ID NO 17
<211> LENGTH: 19
<212> TYPE: DNA
<213> ORGANISM: artificial sequence
<220> FEATURE:
<223> OTHER INFORMATION: primer

<400> SEQUENCE: 17
agctcatcga ccggcaatt                                                       19

<210> SEQ ID NO 18
<211> LENGTH: 23
<212> TYPE: DNA
<213> ORGANISM: artificial sequence
<220> FEATURE:
<223> OTHER INFORMATION: primer

<400> SEQUENCE: 18
cgcactaagg aacttcccgt tat                                                  23

<210> SEQ ID NO 19
<211> LENGTH: 83
<212> TYPE: DNA
<213> ORGANISM: Thauera sp

<400> SEQUENCE: 19
agctcatcga ccggcaattc gtcagcgaac agaccgatct gccgctgctg gtgcgcacgg          60
```
ataacgggaa gttccttagt gcg                                              83

<210> SEQ ID NO 20
<211> LENGTH: 41
<212> TYPE: DNA
<213> ORGANISM: artificial sequence
<220> FEATURE:
<223> OTHER INFORMATION: primer

<400> SEQUENCE: 20
cgtcagcgaa cagaccgacc tgccgctgct ggtgcgcacg g                          41

<210> SEQ ID NO 21
<211> LENGTH: 22
<212> TYPE: DNA
<213> ORGANISM: artificial sequence
<220> FEATURE:
<223> OTHER INFORMATION: primer

<400> SEQUENCE: 21
ggttatcact tcatgaccga gg                                               22

<210> SEQ ID NO 22
<211> LENGTH: 22
<212> TYPE: DNA
<213> ORGANISM: artificial sequence
<220> FEATURE:
<223> OTHER INFORMATION: primer

<400> SEQUENCE: 22
cctcggtcat gaagtgataa cc                                               22

<210> SEQ ID NO 23
<211> LENGTH: 20
<212> TYPE: DNA
<213> ORGANISM: artificial sequence
<220> FEATURE:
<223> OTHER INFORMATION: primer

<400> SEQUENCE: 23
gcatgaccta cctgctggac                                                  20

<210> SEQ ID NO 24
<211> LENGTH: 20
<212> TYPE: DNA
<213> ORGANISM: artificial sequence
<220> FEATURE:
<223> OTHER INFORMATION: primer

<400> SEQUENCE: 24
gtccagcagg taggtcatgc                                                  20

<210> SEQ ID NO 25
<211> LENGTH: 20
<212> TYPE: DNA
<213> ORGANISM: artificial sequence
<220> FEATURE:
<223> OTHER INFORMATION: primer

<400> SEQUENCE: 25
cgatgcgatc atcgacggtc                                                  20

<210> SEQ ID NO 26
<211> LENGTH: 20
<212> TYPE: DNA
<213> ORGANISM: artificial sequence

```
<220> FEATURE:
<223> OTHER INFORMATION: primer

<400> SEQUENCE: 26
gaccgtcgat gatcgcatcg                                                    20

<210> SEQ ID NO 27
<211> LENGTH: 20
<212> TYPE: DNA
<213> ORGANISM: artificial sequence
<220> FEATURE:
<223> OTHER INFORMATION: primer

<400> SEQUENCE: 27
ggacattcat gtgcccgtca                                                    20

<210> SEQ ID NO 28
<211> LENGTH: 20
<212> TYPE: DNA
<213> ORGANISM: artificial sequence
<220> FEATURE:
<223> OTHER INFORMATION: primer

<400> SEQUENCE: 28
tgacgggcac atgaatgtcc                                                    20

<210> SEQ ID NO 29
<211> LENGTH: 1564
<212> TYPE: DNA
<213> ORGANISM: Thauera sp

<400> SEQUENCE: 29
cggcgcaaat ttctcaaggg aagtggtggc ctttgcctgt cgctctccct gtcatcgttt        60
gcgcccgggt ttgtgccggg cgttgtcagc gaggcgctgg cagggacgaa ggtgccatcc       120
tatgcgaaat gggaggatat ctaccgcaac gaatggaagt gggacaaggt cacctggggc       180
tcgcatctga atatctgctg gccgcagggt tcgtgcaagt tctacgtcta tgtccggaac       240
ggtatcgtct ggcgcgagga gcaggcggcg cagacgcccg cctgcaacgc cgactacgtc       300
gattacaacc cgctcggctg tcagaaaggg gctgcattca acaacaacct ctacggcgac       360
gagcgggtca gtatccgct caagcgcgtc ggcgagcgcg gcgaaggcaa gtggaagcgc        420
gtcagctggg acgaggcgac ggccgatatc gccgatgcga tcatcgacgg tctcgaaagc       480
cagggatcgg attctttcat cctggactca ccgcatgtgc acgccggttc agtcgccaac       540
tccggcggct accgcatgac ctacctgctg gacggcgttt ctcccgacaa caatatcgac       600
atcggtgata cctaccaggg agcgttccat accttcggca aaatgcacat ggggtacagc       660
gcggataacc tgctggactc cgaactcatc tttatgacgt gcagcaactg gtcgtacacc       720
tatccgaccg ttatcacttt catgaccgag gcgcgctaca agggcgcgga ggtcgtcgtt       780
gtcgcgcccg acttcagccc cacgaccccg ggcgcggaca ttcatgtgcc cgtcaaagtg       840
gggggggacg cggcgttctg gctcggcgtc agccaggtca tcatcgacga gaagctcatc       900
gaccggaaat tcgtcagcga acagaccgat ctgccgctgc tggtgcgcac ggataacggc       960
aagttcctca gcgcggccga cgtcgacggc ggccacgaga agcagttcta cgtcatcgac      1020
gagaagagtg gtgcgatgcg ccaggcgccg cgcggcacgc tgcggctcga cggtccggtg      1080
gcgttggaag ggaccttcaa ggcgaagctg cgggacggca agacggtcga agtacgcccg      1140
gtctttcaga tgatgaaaga tcagctcgag caggaattca ccccggagaa agccagcgag      1200
```

-continued

```
aagagcggcg tgccggtctc gctgatccgc gaactggggc gcaaggtcgc gaagaagcgt      1260
acgtcgacct acatcggctt caccgcggcg aagagctatc acggcgacct cttcgaacgc      1320
gccatgtacc tggcgctggc gctgagcggc aactggggta agccggggac cggcttctac      1380
tcctgggcct acgccgagga caacatgttc ttcctctccg tcatgaacaa accgacggcg      1440
cagggcggca tggacgaaat ggcgcagatg cagaagtcgt tccacgaccg tctgaagaag      1500
gaggacccga cctccaccga cgagatggcc gacatcgagt tcaccaaggc cgtgaccacc      1560
ctga                                                                   1564
```

<210> SEQ ID NO 30
<211> LENGTH: 2937
<212> TYPE: DNA
<213> ORGANISM: Azoarcus sp.

<400> SEQUENCE: 30

```
atggatgatc tcaagaatac agacgcaatc agaacaggcg tgtcatcggc ctttgaccag        60
aatcggcgtg gctttctgaa gcgaagcggg gcaggcgcac tctcgctttc cttgtcttcg       120
ttcgcagccg gattggtgcc gggtttcgtg aatgcggcgc aggccggaaa acggggggccg      180 acatacgcga cttgggaaga cgtctaccgc aacgagtgga atgggacaa ggtgacatgg        240 ggttcccatt tgaatatttg ctggccccag gggtcatgca aattctacgt ctatgtcaga       300
aacggcatcg tgtggcgcga agagcaggcg cgcaaacgg ccgcgtgtaa tcccgattac        360
gtggattaca acccgtcggg atgccaaaag ggcgcggcgt tcaacaacaa cctctacggc       420
gaggagcggc tcaagtatcc gctcaagcgc gtgggcaagc gcggcgaggg caagtggaag       480
cgcgtcagtt gggacgaggc gacggccgat atcgccgatg cgatcatcga cggcatcgag       540
accgagggga cggatagttt catcctggac tctccgcacg tgcacgccgg ttcggttgcc       600
aactccggcg gctaccgcat gacatacctg ctggacggag tttctcccga caacaacgtg       660
gacatcggcg ataccctactc gggagcgttc cacaccttcg gcaagatgca catggggtat      720
agcgccgata acctgctcga ctccgaactc atcttcatga cttgcagcaa ctggtcgtat       780
acctatccgt ccagttatca cttcatgacc gaggcgcgct acaagggagc cgaggtcgtg       840
gtcgtcgctc ccgacttcaa ccccacgacc ccgggtgcgg accttcatgt tcccgtcaag       900
gtaggccgcg atgcggcgtt ctggctgggg ctttgtcaag tcatgatcga cgagaagctc       960
atcgaccggc aattcgccag cgaacagacc gacctgccgc ttctcgtcag gacggataac      1020
gggaagttcc ttagtgcggc cgacgtcgac ggcggccacg cgaagcagtt ctacgtcatc      1080
gacgagaaga gcggggcgct gcgcgaggcg ccgcgcggca cgctgcggct ggatggtccg      1140
gtggcgctgg aagggacctt cagcgcgaag ctgagggacg cgggacggt ccaggtgcgg       1200 ccggtattcc agctgatgaa ggatcagctc gacaaggaat tcaccccga gaaggccagc      1260 gcgaagagcg gtgcgccggc ctcgctgatc cgcgaactgg ggcgcaaggt cgcgaagaag      1320
cgcacgtcga gctacatcgg cttcaccgcc gcgaagagct atcacggtga cctgttcgaa      1380
cgcagcatgt acttggcgat ggcgctgagc ggcaactggg gtaagccggg gaccggcttc      1440
tactcctggg cctacgccga ggacaacatg ttcttcctcg ccgtgatgaa caagccgacg      1500
gcgcagggcg gcatgaacga atggccgaa atgcagaagt cgttccacga cgtctcaag      1560 aaggggggatc cgacctccac cgacgagatg gccgacatcg aattcacgaa ggccgtgacc     1620
accttgatgg cgccgtacc gccggcgatg tggctgtaca accacgcggg ctacgaccag     1680
ctctacaaca caaggcgtg ggccgatccg tcgctcaaga cgactttcgg cggctacctg     1740
```

-continued

```
aaggaagcgg tggacaaggg ctggtggacg aaggatcacc tgcgtccggc gccggacaag      1800
acgccgcagg tctacatgat gatttcgcac aacccgatcc ggcgcaaacg cagcggcgcg      1860
aagttgtacc ccgaagtgct gttcccgaag ctgaagatga tcttcgcgat ggaagtgcgg      1920
atgtcctcgt cggcgatgta cgcggacatc gtcctgccct gcgcgtggta ctacgagaag      1980
cacgaaatca ccaccccttg cagcggcaac ccgttcttca ccttcgtcga ccgggcggtc      2040
gcgcccccgg ccgagtgcaa ggaggagtgg gaaggcatgg cgctcatcct caagaaggtg      2100
ggcgagcgcg ccaaggccag ggggctcacg gaattcgtcg accattacgg taagaagcgc      2160
cgctacgacg agctgtatag caagttcgtc atggacggtc acctgataac caacgaagac      2220
tgcgtcaagg aaatggtgca gatcaacgaa gcggcggagg tcttccccaa gggctacacc      2280
tacgagcagt tgaagcacga cggccaggtc aagttcacga gcctggggca gtcggtcgcc      2340
aagtacgcct gcggcaacga atacgacccg acgaagccgt tcttcccgtt gcgctggcac      2400
gtcgatgacc ggaaggtgta cccgacgcac acccggcggg cgcagttcta cttcgaccat      2460
gactggtacc tcgaggctgg cgaggcactg ccgacccaca aggatccccc attgataggc      2520
ggtgaccatc cgttccaggt gacgggtggg catccgcggg tgagtatcca ttccacgcat      2580
ctttccaatg cgcacttgtc acggcttcat cgcggccagc cggtggtgca catgaatgac      2640
cacgatgcgg cggagctcgg tatcaaggat ggcgagatgg tgaagatgtt caacgatttc      2700
gccgactgcg aaatcatggc gcgactggcg ccgaacatcc agcccaagca gtgcgtggtt      2760
tatttctggg aggcttatca gtacaagcag tggaagcctt acgacatcat gcttatcggt      2820
atgcccaagg cgcttcatct ggcgggcgga tacgaacagt tccgttatta ctacctgaat      2880
ggaagcccgg cgccggcgac ggaccgaggg gttcgagtaa acatcaaaaa agcgtaa       2937
```

<210> SEQ ID NO 31
<211> LENGTH: 2924
<212> TYPE: DNA
<213> ORGANISM: Azoarcus sp.

<400> SEQUENCE: 31

```
tgacacgaga cgaaatgatt tctgtggagc ccgaagccgc agaattgcag gaccaagaca       60
ggcgcgattt tctgaagcgc agtggggcgg cggtgctctc actttcgctg tcgtcacttg      120
cgaccggcgt ggttccaggc tttctaaagg acgcgcaggc cgggacaaaa gcacccggtt      180
acgcgagttg ggaagacatc tatcgcaaag agtggaaatg gacaaggtc aattgggggt       240 cccatctgaa catttgctgg ccgcagggtt cgtgcaagtt ctacgtatac gtcagaaatg      300
gcatcgtctg gcgtgaagag caggccgccc agacgcccgc gtgtaacgtc gattatgtgg      360
actacaaccc gctggggtgt caaaagggtt cagcattcaa caacaatctg tacggtgacg      420
agcgggtcaa gtatccgcta aagcgtgtcg gcaagcgggg tgaaggcaag tggaagcggg      480
tttcgtggga cgaagccgcc ggcgatatcg cagattctat tatcgacagc ttcgaggccc      540
agggctcgga cggtttcatc ctggatgcgc ctcacgttca cgcgggctcc attgcgtggg      600
gtgccggttt cagaatgacg tatctgatgg acggtgtctc gcccgatatc aacgtggata      660
ttggcgatac ctacatggga gcattccaca cgttcgggaa aatgcatatg gctattcgg       720 cggacaatct gctggatgct gagctcatct tcatgacgtg tagcaattgg tcgtacacct      780
acccgtccag ttaccacttc ctgtcggagg ctcgctacaa gggggccgag gtcgtggtca      840
ttgcgcctga cttcaatccc accacgccgg ccgcagacct tcatgttccg gtccgtgtgg      900
```

```
gcagcgacgc cgctttctgg cttgggcttt cgcaagtcat gatcgacgag aagctgttcg    960
atcgtcagtt tgtgtgtgag cagacggacc tgccgcttct tgtgcgcatg gatacaggga   1020
aattcctcag tgccgaagac gtcgatggcg gtgaagcgaa gcagttctat ttcttcgacg   1080
aaaaagcggg atcggttcgc aaggcgtcca gagcaactct gaaactcgat ttcatgccgg   1140
cccttgaggg cacgttcagt gcgcggctca gaaacggcaa gacgattcag gtgcggacgg   1200
ttttcgaagg actcagggag catctgaagg actacacgcc ggaaaaggcg agtgcgaagt   1260
gcggtgtgcc ggtttcgctg attcgtgagt tgggccgaaa agtcgcgaaa agcgcacgt    1320
gtagctatat cggtttctcg tccgccaaga gctaccacgg cgacctgatg aacgtagtc    1380
tgtttctcgc gatggcactc agcggtaatt ggggcaagcc gggaaccggc gcgttcgcgt   1440
gggcctactc cgacgacaac atggtctacc tcggtgtaat gagcaaaccg accgccaag    1500
gtggcatgga cgagttgcat cagatggccg agggcttcaa caagcgcacg ctcgaggcag   1560
accccacgtc aacagacgaa atggggaata tcgagttcat gaaagtcctt acttcggcgg   1620
tggggttggt gccaccggcg atgtggctgt actaccacgt cggctacgat cagttgtgga   1680
acaacaaggc gtggactgat ccggccctca gaaaatcgtt tggtgcgtat ctggacgagg   1740
cgaaggaaaa gggctggtgg acgaacgacc acatccgccc ggccccagac aagacgcctc   1800
aggtgtacat gctcctgtcg cagaatccga tgagacggaa gcgtagcggt gccaagatgt   1860
tccggacgt tttatttccg aaactcaaga tgatcttcgc cctggaaacg cgcatgtcgt    1920
cgtcagcgat gtatgccgac atcgttctgc cgtgtgcatg gtattacgag aaacacgaga   1980
tgacgacgcc gtgcagcggc aatccgttct tcaccttcgt ggatcggtcg gtagcacctc   2040
cgggtgagtg tcgcgaagaa tgggacgcga ttgcgctcat tctcaagaag gtcggggaac   2100
gcgcggcagc ccgggggctc acggagttca atgatcacaa cgggcgcaag cgccggtacg   2160
acgagttgta caagaagttc acgatggacg ggcacctcct gacgaacgag gactgtttga   2220
aggaaatggt cgacatcaac cgggcggtgg gcgtctttgc gaaggactac acgtacgaaa   2280
agttcaagaa ggaaggtcag accaggttcc tgagcatggg aacgggcgct tccaggtacg   2340
cgcatgcaaa cgaggtcgat gtgaccaagc cgatctatcc gatgcgatgg cacttcgatg   2400
acaagaaggt ctttccgacg catacgcgcc gtgcccagtt ctaccttgac acgactggt    2460
atctcgaagc cggcgagtcg ctgcctaccc ataaggacac gccgatggtg ggggcgacc    2520
atccgttcaa gatcactggc gggcatccgc gtgtgagcat ccattccacg cacctcacga   2580
attcccatct gtccaggctg catcgcggac aaccggtcgt gcacatgaat agcaaggacg   2640
ccgcggagct ggggatcaag gacggcgaca tggcaaagct gttcaacgac tttgccgatt   2700
gcgaaatcat ggtgcgcacg gcgccgaacg ttcagccgaa gcagtgcatt gtctatttct   2760
gggacgcgca tcagtacaaa ggctggaaac cctacgacat cctgctcatc ggaatgccca   2820
agccactgca cttggcgggc ggttacgaac agtttcgcta ctacttcatg aacggaagtc   2880
cggccccgt cacggaccgt ggcgtgcggg taagcatcaa gtaa                    2924
```

<210> SEQ ID NO 32
<211> LENGTH: 521
<212> TYPE: PRT
<213> ORGANISM: Thauera sp.

<400> SEQUENCE: 32

Arg Arg Lys Phe Leu Lys Gly Ser Gly Gly Leu Cys Leu Ser Leu Ser
1               5                   10                  15

```
Leu Ser Ser Phe Ala Pro Gly Phe Val Pro Gly Val Ser Glu Ala
         20                  25                  30

Leu Ala Gly Thr Lys Val Pro Ser Tyr Ala Lys Trp Glu Asp Ile Tyr
             35                  40                  45

Arg Asn Glu Trp Lys Trp Asp Lys Val Thr Trp Gly Ser His Leu Asn
 50                  55                  60

Ile Cys Trp Pro Gln Gly Ser Cys Lys Phe Tyr Val Tyr Val Arg Asn
 65                  70                  75                  80

Gly Ile Val Trp Arg Glu Gln Ala Ala Gln Thr Ala Ala Cys Asn
                 85                  90                  95

Ala Asp Tyr Val Asp Tyr Asn Pro Leu Gly Cys Gln Lys Gly Ala Ala
             100                 105                 110

Phe Asn Asn Asn Leu Tyr Gly Asp Glu Arg Val Lys Tyr Pro Leu Lys
             115                 120                 125

Arg Val Gly Glu Arg Gly Glu Gly Lys Trp Lys Arg Val Ser Trp Asp
 130                 135                 140

Glu Ala Thr Ala Asp Ile Ala Asp Ala Ile Ile Asp Gly Leu Glu Ser
 145                 150                 155                 160

Gln Gly Ser Asp Ser Phe Ile Leu Asp Ser Pro His Val His Ala Gly
                 165                 170                 175

Ser Val Ala Asn Ser Gly Gly Tyr Arg Met Thr Tyr Leu Leu Asp Gly
             180                 185                 190

Val Ser Pro Asp Asn Asn Ile Asp Ile Gly Asp Thr Tyr Gln Gly Ala
             195                 200                 205

Phe His Thr Phe Gly Lys Met His Met Gly Tyr Ser Ala Asp Asn Leu
 210                 215                 220

Leu Asp Ser Glu Leu Ile Phe Met Thr Cys Ser Asn Trp Ser Tyr Thr
 225                 230                 235                 240

Tyr Pro Thr Gly Tyr His Phe Met Thr Glu Ala Arg Tyr Lys Gly Ala
             245                 250                 255

Glu Val Val Val Val Ala Pro Asp Phe Ser Pro Thr Thr Pro Gly Ala
             260                 265                 270

Asp Ile His Val Pro Val Lys Val Gly Gly Asp Ala Ala Phe Trp Leu
             275                 280                 285

Gly Val Ser Gln Val Ile Ile Asp Glu Lys Leu Ile Asp Arg Lys Phe
             290                 295                 300

Val Ser Glu Gln Thr Asp Leu Pro Leu Leu Val Arg Thr Asp Asn Gly
 305                 310                 315                 320

Lys Phe Leu Ser Ala Ala Asp Val Asp Gly Gly His Glu Lys Gln Phe
                 325                 330                 335

Tyr Val Ile Asp Glu Lys Ser Gly Ala Met Arg Gln Ala Pro Arg Gly
             340                 345                 350

Thr Leu Arg Leu Asp Gly Pro Val Ala Leu Glu Gly Thr Phe Lys Ala
             355                 360                 365

Lys Leu Arg Asp Gly Lys Thr Val Glu Val Arg Pro Val Phe Gln Met
             370                 375                 380

Met Lys Asp Gln Leu Glu Gln Glu Phe Thr Pro Glu Lys Ala Ser Glu
 385                 390                 395                 400

Lys Ser Gly Val Pro Val Ser Leu Ile Arg Glu Leu Gly Arg Lys Val
                 405                 410                 415

Ala Lys Lys Arg Thr Ser Thr Tyr Ile Gly Phe Thr Ala Ala Lys Ser
             420                 425                 430

Tyr His Gly Asp Leu Phe Glu Arg Ala Met Tyr Leu Ala Leu Ala Leu
```

```
                435                 440                 445
Ser Gly Asn Trp Gly Lys Pro Gly Thr Gly Phe Tyr Ser Trp Ala Tyr
    450                 455                 460

Ala Glu Asp Asn Met Phe Phe Leu Ser Val Met Asn Lys Pro Thr Ala
465                 470                 475                 480

Gln Gly Gly Met Asp Glu Met Ala Gln Met Gln Lys Ser Phe His Asp
                485                 490                 495

Arg Leu Lys Lys Glu Asp Pro Thr Ser Thr Asp Glu Met Ala Asp Ile
                500                 505                 510

Glu Phe Thr Lys Ala Val Thr Thr Leu
                515                 520

<210> SEQ ID NO 33
<211> LENGTH: 976
<212> TYPE: PRT
<213> ORGANISM: Azoarcus sp.

<400> SEQUENCE: 33

Met Thr Arg Asp Glu Met Ile Ser Val Glu Pro Glu Ala Ala Glu Leu
1               5                   10                  15

Gln Asp Gln His Arg Arg Asp Phe Leu Lys Arg Ser Gly Ala Ala Val
                20                  25                  30

Leu Ser Leu Ser Leu Ser Ser Leu Ala Thr Gly Val Val Pro Gly Phe
            35                  40                  45

Leu Lys Asp Ala Gln Ala Gly Thr Lys Ala Pro Gly Tyr Ala Ser Trp
    50                  55                  60

Glu Asp Ile Tyr Arg Lys Glu Trp Lys Trp Asp Lys Val Asn Trp Gly
65              70                  75                  80

Ser His Leu Asn Ile Cys Trp Pro Gln Gly Ser Cys Lys Phe Tyr Val
                85                  90                  95

Tyr Val Arg Asn Gly Ile Val Trp Arg Glu Glu Gln Ala Ala Gln Thr
                100                 105                 110

Pro Ala Cys Asn Val Asp Tyr Val Asp Tyr Asn Pro Leu Gly Cys Gln
            115                 120                 125

Lys Gly Ser Ala Phe Asn Asn Asn Leu Tyr Gly Asp Glu Arg Val Lys
    130                 135                 140

Tyr Pro Leu Lys Arg Val Gly Lys Arg Gly Glu Gly Lys Trp Lys Arg
145             150                 155                 160

Val Ser Trp Asp Glu Ala Ala Gly Asp Ile Ala Asp Ser Ile Ile Asp
                165                 170                 175

Ser Phe Glu Ala Gln Gly Ser Asp Gly Phe Ile Leu Asp Ala Pro His
            180                 185                 190

Val His Ala Gly Ser Ile Ala Trp Gly Ala Gly Phe Arg Met Thr Tyr
        195                 200                 205

Leu Met Asp Gly Val Ser Pro Asp Ile Asn Val Asp Ile Gly Asp Thr
    210                 215                 220

Tyr Met Gly Ala Phe His Thr Phe Gly Lys Met His Met Gly Tyr Ser
225             230                 235                 240

Ala Asp Asn Leu Leu Asp Ala Glu Leu Ile Phe Met Thr Cys Ser Asn
                245                 250                 255

Trp Ser Tyr Thr Tyr Pro Ser Ser Tyr His Phe Leu Ser Glu Ala Arg
            260                 265                 270

Tyr Lys Gly Ala Glu Val Val Val Ile Ala Pro Asp Phe Asn Pro Thr
    275                 280                 285
```

```
Thr Pro Ala Ala Asp Leu His Val Pro Val Arg Val Gly Ser Asp Ala
290                 295                 300

Ala Phe Trp Leu Gly Leu Ser Gln Val Met Ile Asp Glu Lys Leu Phe
305                 310                 315                 320

Asp Arg Gln Phe Val Cys Glu Gln Thr Asp Leu Pro Leu Leu Val Arg
                325                 330                 335

Met Asp Thr Gly Lys Phe Leu Ser Ala Glu Asp Val Asp Gly Gly Glu
            340                 345                 350

Ala Lys Gln Phe Tyr Phe Phe Asp Glu Lys Ala Gly Ser Val Arg Lys
        355                 360                 365

Ala Ser Arg Gly Thr Leu Lys Leu Asp Phe Met Pro Ala Leu Glu Gly
    370                 375                 380

Thr Phe Ser Ala Arg Leu Lys Asn Gly Lys Thr Ile Gln Val Arg Thr
385                 390                 395                 400

Val Phe Glu Gly Leu Arg Glu His Leu Lys Asp Tyr Thr Pro Glu Lys
                405                 410                 415

Ala Ser Ala Lys Cys Gly Val Pro Val Ser Leu Ile Arg Glu Leu Gly
            420                 425                 430

Arg Lys Val Ala Lys Arg Thr Cys Ser Tyr Ile Gly Phe Ser Ser
        435                 440                 445

Ala Lys Ser Tyr His Gly Asp Leu Met Glu Arg Ser Leu Phe Leu Ala
    450                 455                 460

Met Ala Leu Ser Gly Asn Trp Gly Lys Pro Gly Thr Gly Ala Phe Ala
465                 470                 475                 480

Trp Ala Tyr Ser Asp Asp Asn Met Val Tyr Leu Gly Val Met Ser Lys
                485                 490                 495

Pro Thr Ala Gln Gly Gly Met Asp Glu Leu His Gln Met Ala Glu Gly
            500                 505                 510

Phe Asn Lys Arg Thr Leu Glu Ala Asp Pro Thr Ser Thr Asp Glu Met
        515                 520                 525

Gly Asn Ile Glu Phe Met Lys Val Val Thr Ser Ala Val Gly Leu Val
    530                 535                 540

Pro Pro Ala Met Trp Leu Tyr Tyr His Val Gly Tyr Asp Gln Leu Trp
545                 550                 555                 560

Asn Asn Lys Ala Trp Thr Asp Pro Ala Leu Lys Lys Ser Phe Gly Ala
                565                 570                 575

Tyr Leu Asp Glu Ala Lys Glu Lys Gly Trp Trp Thr Asn Asp His Ile
            580                 585                 590

Arg Pro Ala Pro Asp Lys Thr Pro Gln Val Tyr Met Leu Leu Ser Gln
        595                 600                 605

Asn Pro Met Arg Arg Lys Arg Ser Gly Ala Lys Met Phe Pro Asp Val
    610                 615                 620

Leu Phe Pro Lys Leu Lys Met Ile Phe Ala Leu Glu Thr Arg Met Ser
625                 630                 635                 640

Ser Ser Ala Met Tyr Ala Asp Ile Val Leu Pro Cys Ala Trp Tyr Tyr
                645                 650                 655

Glu Lys His Glu Met Thr Thr Pro Cys Ser Gly Asn Pro Phe Phe Thr
            660                 665                 670

Phe Val Asp Arg Ser Val Ala Pro Pro Gly Glu Cys Arg Glu Glu Trp
        675                 680                 685

Asp Ala Ile Ala Leu Ile Leu Lys Lys Val Gly Glu Arg Ala Ala Ala
    690                 695                 700

Arg Gly Leu Thr Glu Phe Asn Asp His Asn Gly Arg Lys Arg Arg Tyr
```

```
                705                 710                 715                 720
Asp Glu Leu Tyr Lys Lys Phe Thr Met Asp Gly His Leu Leu Thr Asn
                    725                 730                 735
Glu Asp Cys Leu Lys Glu Met Val Asp Ile Asn Arg Ala Val Gly Val
                740                 745                 750
Phe Ala Lys Asp Tyr Thr Tyr Glu Lys Phe Lys Lys Glu Gly Gln Thr
            755                 760                 765
Arg Phe Leu Ser Met Gly Thr Gly Val Ser Arg Tyr Ala His Ala Asn
        770                 775                 780
Glu Val Asp Val Thr Lys Pro Ile Tyr Pro Met Arg Trp His Phe Asp
785                 790                 795                 800
Asp Lys Lys Val Phe Pro Thr His Thr Arg Arg Ala Gln Phe Tyr Leu
                805                 810                 815
Asp His Asp Trp Tyr Leu Glu Ala Gly Glu Ser Leu Pro Thr His Lys
                820                 825                 830
Asp Thr Pro Met Val Gly Gly Asp His Pro Phe Lys Ile Thr Gly Gly
                835                 840                 845
His Pro Arg Val Ser Ile His Ser Thr His Leu Thr Asn Ser His Leu
            850                 855                 860
Ser Arg Leu His Arg Gly Gln Pro Val Val His Met Asn Ser Lys Asp
865                 870                 875                 880
Ala Ala Glu Leu Gly Ile Lys Asp Gly Asp Met Ala Lys Leu Phe Asn
                885                 890                 895
Asp Phe Ala Asp Cys Glu Ile Met Val Arg Thr Ala Pro Asn Val Gln
                900                 905                 910
Pro Lys Gln Cys Ile Val Tyr Phe Trp Asp Ala His Gln Tyr Lys Gly
            915                 920                 925
Trp Lys Pro Tyr Asp Ile Leu Leu Ile Gly Met Pro Lys Pro Leu His
        930                 935                 940
Leu Ala Gly Gly Tyr Glu Gln Phe Arg Tyr Tyr Phe Met Asn Gly Ser
945                 950                 955                 960
Pro Ala Pro Val Thr Asp Arg Gly Val Arg Val Ser Ile Lys Lys Ala
                965                 970                 975

<210> SEQ ID NO 34
<211> LENGTH: 974
<212> TYPE: PRT
<213> ORGANISM: azoarcus sp.

<400> SEQUENCE: 34

Met Thr Arg Asp Glu Met Ile Ser Val Glu Pro Glu Ala Ala Glu Leu
1               5                   10                  15
Gln Asp Gln Asp Arg Arg Asp Phe Leu Lys Arg Ser Gly Ala Ala Val
                20                  25                  30
Leu Ser Leu Ser Leu Ser Ser Leu Ala Thr Gly Val Val Pro Gly Phe
            35                  40                  45
Leu Lys Asp Ala Gln Ala Gly Thr Lys Ala Pro Gly Tyr Ala Ser Trp
        50                  55                  60
Glu Asp Ile Tyr Arg Lys Glu Trp Lys Trp Asp Lys Val Asn Trp Gly
65                  70                  75                  80
Ser His Leu Asn Ile Cys Trp Pro Gln Gly Ser Cys Lys Phe Tyr Val
                85                  90                  95
Tyr Val Arg Asn Gly Ile Val Trp Arg Glu Glu Gln Ala Ala Gln Thr
                100                 105                 110
```

Pro Ala Cys Asn Val Asp Tyr Val Asp Tyr Asn Pro Leu Gly Cys Gln
        115                 120                 125

Lys Gly Ser Ala Phe Asn Asn Asn Leu Tyr Gly Asp Glu Arg Val Lys
    130                 135                 140

Tyr Pro Leu Lys Arg Val Gly Lys Arg Gly Glu Gly Lys Trp Lys Arg
145                 150                 155                 160

Val Ser Trp Asp Glu Ala Ala Gly Asp Ile Ala Asp Ser Ile Ile Asp
                165                 170                 175

Ser Phe Glu Ala Gln Gly Ser Asp Gly Phe Ile Leu Asp Ala Pro His
            180                 185                 190

Val His Ala Gly Ser Ile Ala Trp Gly Ala Gly Phe Arg Met Thr Tyr
        195                 200                 205

Leu Met Asp Gly Val Ser Pro Asp Ile Asn Val Asp Ile Gly Asp Thr
    210                 215                 220

Tyr Met Gly Ala Phe His Thr Phe Gly Lys Met His Met Gly Tyr Ser
225                 230                 235                 240

Ala Asp Asn Leu Leu Asp Ala Glu Leu Ile Phe Met Thr Cys Ser Asn
                245                 250                 255

Trp Ser Tyr Thr Tyr Pro Ser Ser Tyr His Phe Leu Ser Glu Ala Arg
            260                 265                 270

Tyr Lys Gly Ala Glu Val Val Ile Ala Pro Asp Phe Asn Pro Thr
        275                 280                 285

Thr Pro Ala Ala Asp Leu His Val Pro Val Arg Val Gly Ser Asp Ala
    290                 295                 300

Ala Phe Trp Leu Gly Leu Ser Gln Val Met Ile Asp Glu Lys Leu Phe
305                 310                 315                 320

Asp Arg Gln Phe Val Cys Glu Gln Thr Asp Leu Pro Leu Leu Val Arg
                325                 330                 335

Met Asp Thr Gly Lys Phe Leu Ser Ala Glu Asp Val Asp Gly Gly Glu
            340                 345                 350

Ala Lys Gln Phe Tyr Phe Phe Asp Glu Lys Ala Gly Ser Val Arg Lys
        355                 360                 365

Ala Ser Arg Ala Thr Leu Lys Leu Asp Phe Met Pro Ala Leu Glu Gly
    370                 375                 380

Thr Phe Ser Ala Arg Leu Lys Asn Gly Lys Thr Ile Gln Val Arg Thr
385                 390                 395                 400

Val Phe Glu Gly Leu Arg Glu His Leu Lys Asp Tyr Thr Pro Glu Lys
                405                 410                 415

Ala Ser Ala Lys Cys Gly Val Pro Val Ser Leu Ile Arg Glu Leu Gly
            420                 425                 430

Arg Lys Val Ala Lys Arg Thr Cys Ser Tyr Ile Gly Phe Ser Ser
        435                 440                 445

Ala Lys Ser Tyr His Gly Asp Leu Met Glu Arg Ser Leu Phe Leu Ala
    450                 455                 460

Met Ala Leu Ser Gly Asn Trp Gly Lys Pro Gly Thr Gly Ala Phe Ala
465                 470                 475                 480

Trp Ala Tyr Ser Asp Asp Asn Met Val Tyr Leu Gly Val Met Ser Lys
                485                 490                 495

Pro Thr Ala Gln Gly Gly Met Asp Glu Leu His Gln Met Ala Glu Gly
            500                 505                 510

Phe Asn Lys Arg Thr Leu Glu Ala Asp Pro Thr Ser Thr Asp Glu Met
        515                 520                 525

Gly Asn Ile Glu Phe Met Lys Val Leu Thr Ser Ala Val Gly Leu Val

```
                530                 535                 540
Pro Pro Ala Met Trp Leu Tyr Tyr His Val Gly Tyr Asp Gln Leu Trp
545                 550                 555                 560

Asn Asn Lys Ala Trp Thr Asp Pro Ala Leu Lys Lys Ser Phe Gly Ala
                565                 570                 575

Tyr Leu Asp Glu Ala Lys Glu Lys Gly Trp Trp Thr Asn Asp His Ile
                580                 585                 590

Arg Pro Ala Pro Asp Lys Thr Pro Gln Val Tyr Met Leu Leu Ser Gln
                595                 600                 605

Asn Pro Met Arg Arg Lys Arg Ser Gly Ala Lys Met Phe Pro Asp Val
610                 615                 620

Leu Phe Pro Lys Leu Lys Met Ile Phe Ala Leu Glu Thr Arg Met Ser
625                 630                 635                 640

Ser Ser Ala Met Tyr Ala Asp Ile Val Leu Pro Cys Ala Trp Tyr Tyr
                645                 650                 655

Glu Lys His Glu Met Thr Thr Pro Cys Ser Gly Asn Pro Phe Phe Thr
                660                 665                 670

Phe Val Asp Arg Ser Val Ala Pro Pro Gly Glu Cys Arg Glu Glu Trp
                675                 680                 685

Asp Ala Ile Ala Leu Ile Leu Lys Lys Val Gly Glu Arg Ala Ala Ala
                690                 695                 700

Arg Gly Leu Thr Glu Phe Asn Asp His Asn Gly Arg Lys Arg Arg Tyr
705                 710                 715                 720

Asp Glu Leu Tyr Lys Lys Phe Thr Met Asp Gly His Leu Leu Thr Asn
                725                 730                 735

Glu Asp Cys Leu Lys Glu Met Val Asp Ile Asn Arg Ala Val Gly Val
                740                 745                 750

Phe Ala Lys Asp Tyr Thr Tyr Glu Lys Phe Lys Lys Glu Gly Gln Thr
                755                 760                 765

Arg Phe Leu Ser Met Gly Thr Gly Ala Ser Arg Tyr Ala His Ala Asn
770                 775                 780

Glu Val Asp Val Thr Lys Pro Ile Tyr Pro Met Arg Trp His Phe Asp
785                 790                 795                 800

Asp Lys Lys Val Phe Pro Thr His Thr Arg Arg Ala Gln Phe Tyr Leu
                805                 810                 815

Asp His Asp Trp Tyr Leu Glu Ala Gly Glu Ser Leu Pro Thr His Lys
                820                 825                 830

Asp Thr Pro Met Val Gly Gly Asp His Pro Phe Lys Ile Thr Gly Gly
                835                 840                 845

His Pro Arg Val Ser Ile His Ser Thr His Leu Thr Asn Ser His Leu
850                 855                 860

Ser Arg Leu His Arg Gly Gln Pro Val Val His Met Asn Ser Lys Asp
865                 870                 875                 880

Ala Ala Glu Leu Gly Ile Lys Asp Gly Asp Met Ala Lys Leu Phe Asn
                885                 890                 895

Asp Phe Ala Asp Cys Glu Ile Met Val Arg Thr Ala Pro Asn Val Gln
                900                 905                 910

Pro Lys Gln Cys Ile Val Tyr Phe Trp Asp Ala His Gln Tyr Lys Gly
                915                 920                 925

Trp Lys Pro Tyr Asp Ile Leu Leu Ile Gly Met Pro Lys Pro Leu His
                930                 935                 940

Leu Ala Gly Gly Tyr Glu Gln Phe Arg Tyr Tyr Phe Met Asn Gly Ser
945                 950                 955                 960
```

Pro Ala Pro Val Thr Asp Arg Gly Val Arg Val Ser Ile Lys
            965                 970

<210> SEQ ID NO 35
<211> LENGTH: 974
<212> TYPE: PRT
<213> ORGANISM: Azoarcus sp.

<400> SEQUENCE: 35

Met Thr Arg Asp Glu Met Ile Ser Val Glu Pro Ala Ala Glu Leu
1               5                   10                  15

Gln Asp Gln Asp Arg Arg Asp Phe Leu Lys Arg Ser Gly Ala Ala Val
            20                  25                  30

Leu Ser Leu Ser Leu Ser Ser Leu Ala Thr Gly Val Val Pro Gly Phe
        35                  40                  45

Leu Lys Asp Ala Gln Ala Gly Thr Lys Ala Pro Gly Tyr Ala Ser Trp
    50                  55                  60

Glu Asp Ile Tyr Arg Lys Glu Trp Lys Trp Asp Lys Val Asn Trp Gly
65                  70                  75                  80

Ser His Leu Asn Ile Cys Trp Pro Gln Gly Ser Cys Lys Phe Tyr Val
                85                  90                  95

Tyr Val Arg Asn Gly Ile Val Trp Arg Glu Glu Gln Ala Ala Gln Thr
            100                 105                 110

Pro Ala Cys Asn Val Asp Tyr Val Asp Tyr Asn Pro Leu Gly Cys Gln
        115                 120                 125

Lys Gly Ser Ala Phe Asn Asn Asn Leu Tyr Gly Asp Glu Arg Val Lys
    130                 135                 140

Tyr Pro Leu Lys Arg Val Gly Lys Arg Gly Glu Gly Lys Trp Lys Arg
145                 150                 155                 160

Val Ser Trp Asp Glu Ala Ala Gly Asp Ile Ala Asp Ser Ile Ile Asp
                165                 170                 175

Ser Phe Glu Ala Gln Gly Ser Asp Gly Phe Ile Leu Asp Ala Pro His
            180                 185                 190

Val His Ala Gly Ser Ile Ala Trp Gly Ala Gly Phe Arg Met Thr Tyr
        195                 200                 205

Leu Met Asp Gly Val Ser Pro Asp Ile Asn Val Asp Ile Gly Asp Thr
    210                 215                 220

Tyr Met Gly Ala Phe His Thr Phe Gly Lys Met His Met Gly Tyr Ser
225                 230                 235                 240

Ala Asp Asn Leu Leu Asp Ala Glu Leu Ile Phe Met Thr Cys Ser Asn
                245                 250                 255

Trp Ser Thr Tyr Pro Ser Ser Tyr His Phe Leu Ser Glu Ala Arg
            260                 265                 270

Tyr Lys Gly Ala Glu Val Val Ile Ala Pro Asp Phe Asn Pro Thr
        275                 280                 285

Thr Pro Ala Ala Asp Leu His Val Pro Val Arg Val Gly Ser Asp Ala
    290                 295                 300

Ala Phe Trp Leu Gly Leu Ser Gln Val Met Ile Asp Glu Lys Leu Phe
305                 310                 315                 320

Asp Arg Gln Phe Val Cys Glu Gln Thr Asp Leu Pro Leu Leu Val Arg
                325                 330                 335

Met Asp Thr Gly Lys Phe Leu Ser Ala Glu Asp Val Asp Gly Gly Glu
            340                 345                 350

Ala Lys Gln Phe Tyr Phe Phe Asp Glu Lys Ala Gly Ser Val Arg Lys

-continued

```
              355                 360                 365
Ala Ser Arg Ala Thr Leu Lys Leu Asp Phe Met Pro Ala Leu Glu Gly
            370                 375                 380

Thr Phe Ser Ala Arg Leu Lys Asn Gly Lys Thr Ile Gln Val Arg Thr
385                 390                 395                 400

Val Phe Glu Gly Leu Arg Glu His Leu Lys Asp Tyr Thr Pro Glu Lys
                405                 410                 415

Ala Ser Ala Lys Cys Gly Val Pro Val Ser Leu Ile Arg Glu Leu Gly
                420                 425                 430

Arg Lys Val Ala Lys Arg Thr Cys Ser Tyr Ile Gly Phe Ser Ser
            435                 440                 445

Ala Lys Ser Tyr His Gly Asp Leu Met Glu Arg Ser Leu Phe Leu Ala
        450                 455                 460

Met Ala Leu Ser Gly Asn Trp Gly Lys Pro Gly Thr Gly Ala Phe Ala
465                 470                 475                 480

Trp Ala Tyr Ser Asp Asp Asn Met Val Tyr Leu Gly Val Met Ser Lys
                485                 490                 495

Pro Thr Ala Gln Gly Gly Met Asp Glu Leu His Gln Met Ala Glu Gly
                500                 505                 510

Phe Asn Lys Arg Thr Leu Glu Ala Asp Pro Thr Ser Thr Asp Glu Met
            515                 520                 525

Gly Asn Ile Glu Phe Met Lys Val Leu Thr Ser Ala Val Gly Leu Val
        530                 535                 540

Pro Pro Ala Met Trp Leu Tyr Tyr His Val Gly Tyr Asp Gln Leu Trp
545                 550                 555                 560

Asn Asn Lys Ala Trp Thr Asp Pro Ala Leu Lys Lys Ser Phe Gly Ala
                565                 570                 575

Tyr Leu Asp Glu Ala Lys Glu Lys Gly Trp Trp Thr Asn Asp His Ile
            580                 585                 590

Arg Pro Ala Pro Asp Lys Thr Pro Gln Val Tyr Met Leu Leu Ser Gln
        595                 600                 605

Asn Pro Met Arg Arg Lys Arg Ser Gly Ala Lys Met Phe Pro Asp Val
    610                 615                 620

Leu Phe Pro Lys Leu Lys Met Ile Phe Ala Leu Glu Thr Arg Met Ser
625                 630                 635                 640

Ser Ser Ala Met Tyr Ala Asp Ile Val Leu Pro Cys Ala Trp Tyr Tyr
                645                 650                 655

Glu Lys His Glu Met Thr Thr Pro Cys Ser Gly Asn Pro Phe Phe Thr
            660                 665                 670

Phe Val Asp Arg Ser Val Ala Pro Pro Gly Glu Cys Arg Glu Glu Trp
        675                 680                 685

Asp Ala Ile Ala Leu Ile Leu Lys Lys Val Gly Glu Arg Ala Ala Ala
    690                 695                 700

Arg Gly Leu Thr Glu Phe Asn Asp His Asn Gly Arg Lys Arg Arg Tyr
705                 710                 715                 720

Asp Glu Leu Tyr Lys Lys Phe Thr Met Asp Gly His Leu Leu Thr Asn
                725                 730                 735

Glu Asp Cys Leu Lys Glu Met Val Asp Ile Asn Arg Ala Val Gly Val
            740                 745                 750

Phe Ala Lys Asp Tyr Thr Tyr Glu Lys Phe Lys Lys Glu Gly Gln Thr
        755                 760                 765

Arg Phe Leu Ser Met Gly Thr Gly Ala Ser Arg Tyr Ala His Ala Asn
    770                 775                 780
```

-continued

```
Glu Val Asp Val Thr Lys Pro Ile Tyr Pro Met Arg Trp His Phe Asp
785                 790                 795                 800

Asp Lys Lys Val Phe Pro Thr His Thr Arg Arg Ala Gln Phe Tyr Leu
                805                 810                 815

Asp His Asp Trp Tyr Leu Glu Ala Gly Glu Ser Leu Pro Thr His Lys
            820                 825                 830

Asp Thr Pro Met Val Gly Gly Asp His Pro Phe Lys Ile Thr Gly Gly
        835                 840                 845

His Pro Arg Val Ser Ile His Ser Thr His Leu Thr Asn Ser His Leu
850                 855                 860

Ser Arg Leu His Arg Gly Gln Pro Val Val His Met Asn Ser Lys Asp
865                 870                 875                 880

Ala Ala Glu Leu Gly Ile Lys Asp Gly Asp Met Ala Lys Leu Phe Asn
                885                 890                 895

Asp Phe Ala Asp Cys Glu Ile Met Val Arg Thr Ala Pro Asn Val Gln
            900                 905                 910

Pro Lys Gln Cys Ile Val Tyr Phe Trp Asp Ala His Gln Tyr Lys Gly
        915                 920                 925

Trp Lys Pro Tyr Asp Ile Leu Leu Ile Gly Met Pro Lys Pro Leu His
    930                 935                 940

Leu Ala Gly Gly Tyr Glu Gln Phe Arg Tyr Tyr Phe Met Asn Gly Ser
945                 950                 955                 960

Pro Ala Pro Val Thr Asp Arg Gly Val Arg Val Ser Ile Lys
                965                 970

<210> SEQ ID NO 36
<211> LENGTH: 20
<212> TYPE: DNA
<213> ORGANISM: artificial sequence
<220> FEATURE:
<223> OTHER INFORMATION: primer

<400> SEQUENCE: 36
ctcatcgacc ggaaattcgt                                              20

<210> SEQ ID NO 37
<211> LENGTH: 20
<212> TYPE: DNA
<213> ORGANISM: artificial sequence
<220> FEATURE:
<223> OTHER INFORMATION: primer

<400> SEQUENCE: 37
cgctgaggaa cttgccgtta                                              20

<210> SEQ ID NO 38
<211> LENGTH: 15
<212> TYPE: DNA
<213> ORGANISM: artificial sequence
<220> FEATURE:
<223> OTHER INFORMATION: primer

<400> SEQUENCE: 38
ccgatctgcc gctgc                                                   15

<210> SEQ ID NO 39
<211> LENGTH: 18
<212> TYPE: DNA
<213> ORGANISM: artificial sequence
<220> FEATURE:
```

```
<223> OTHER INFORMATION: primer

<400> SEQUENCE: 39
cggtgaatac gttcycgg                                                 18

<210> SEQ ID NO 40
<211> LENGTH: 19
<212> TYPE: DNA
<213> ORGANISM: artificial sequence
<220> FEATURE:
<223> OTHER INFORMATION: primer

<400> SEQUENCE: 40
cttgtacaca ccgcccgtc                                                19
```

What is claimed is:

1. An oil recovery enhancing composition comprising:
   (a) *Thauera* strain AL9:8 (ATCC No. PTA 9497);
   (b) one or more electron acceptors; and
   (c) at least one carbon source.

2. The composition of claim 1, wherein said at least one carbon source comprises oil or an oil component.

3. The composition of claim 1, further comprising one or more additional microorganisms.

4. The composition of claim 3, wherein said one or more additional microorganisms are capable of growing on oil under denitrifying conditions.

5. The composition of claim 4, wherein said one or more additional microorganisms comprises the bacterial isolate *Pseudomonas stutzeri* LH4:15 (ATCC No. PTA-8823).

6. A method for improving oil recovery from an oil reservoir comprising:
   (a) providing a composition comprising as bacterial isolate *Thauera* strain AL9:8 (ATCC No. PTA 9497), and minimal medium comprising simple nitrates capable of promoting the growth of said isolate; and
   (b) inoculating said reservoir with the composition of (a); wherein growth of said isolate, under denitrifying conditions, in the oil reservoir promotes improved oil recovery.

7. The method of claim 6, wherein the composition of (a) further comprises one or more additional microorganisms capable of growing on oil under denitrifying conditions.

8. The method of claim 7, wherein said one or more additional microorganisms comprises the bacterial isolate *Pseudomonas stutzeri* LH4:15 (ATCC No. PTA-8823).

9. The method of claim 6, wherein oil recovery is improved by growth of bacterial isolate *Thauera* strain AL9:8 (ATCC No. PTA 9497) wherein said growth results in one or more of the following: (a) alteration of the permeability of the subterranean formation to improve water sweep efficiency; (b) production of biosurfactants which decrease surface and interfacial tensions; (c) mediation of changes in wettability; (d) production of polymers which facilitate mobility of petroleum; (e) generation of gases that increase formation pressure; and (f) reduction of oil viscosity.

10. The method of claim 9, wherein the gases of (e) comprise $CO_2$.

11. A method for promoting hydrocarbon bioremediation comprising applying bacterial isolate *Thauera* strain AL9:8 (ATCC No. PTA 9497) to an area contaminated with hydrocarbons.

12. The method of claim 11, further comprising applying one or more additional microorganism.

* * * * *